United States Patent
Sheng et al.

(10) Patent No.: US 11,236,077 B2
(45) Date of Patent: Feb. 1, 2022

(54) FRUQUINTINIB EUTECTIC CRYSTAL, PREPARATION METHOD THEREFOR, COMPOSITION, AND USES THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN)

(73) Assignee: Hangzhou Solipharma Co., Ltd., Zhejiang (CN)

( * ) Notice: Subject to any disclaimer, the term of this patent is extended or adjusted under 35 U.S.C. 154(b) by 0 days.

(21) Appl. No.: 17/044,243

(22) PCT Filed: Mar. 30, 2018

(86) PCT No.: PCT/CN2018/081255
§ 371 (c)(1),
(2) Date: Sep. 30, 2020

(87) PCT Pub. No.: WO2019/183916
PCT Pub. Date: Oct. 3, 2019

(65) Prior Publication Data
US 2021/0155613 A1  May 27, 2021

(51) Int. Cl.
*C07D 407/12* (2006.01)
*C07C 55/08* (2006.01)
*C07C 57/145* (2006.01)
*C07D 275/03* (2006.01)

(52) U.S. Cl.
CPC .......... *C07D 407/12* (2013.01); *C07C 55/08* (2013.01); *C07C 57/145* (2013.01); *C07D 275/03* (2013.01); *C07B 2200/13* (2013.01)

(58) Field of Classification Search
CPC .... C07D 407/12; C07D 275/03; C07C 55/08; C07C 57/145
See application file for complete search history.

(56) References Cited

FOREIGN PATENT DOCUMENTS

| | | | |
|---|---|---|---|
| CN | 101575333 | * | 11/2009 |
| CN | 101575333 | A | 11/2009 |
| CN | 105461702 | A | 4/2016 |
| CN | 105777721 | A | 7/2016 |
| CN | 105777722 | A | 7/2016 |
| CN | 105777723 | A | 7/2016 |
| WO | WO-2009137797 | A2 | 11/2009 |

OTHER PUBLICATIONS

Wang, Progress in Pharmaceutical Sciences, VOl 37(3), 12-130, 2013. (Year: 2013).*
Gao, Y., et al., "Pharmaceuticals Cocrystals," *Progress in Chemistry* 22(5):829-836, Chinese Academy of Sciences, China (May 2010).
International Search Report and Written Opinion for International Application No. PCT/CN2018/081255, State Intellectual Property Office of the P.R. China, China, dated Jan. 9, 2019, 24 pages (with English Translation).
Wang, Y., et al., "Recent Research Advances of Pharmaceutical Cocrystals," *Progress in Pharmaceutical Sciences* 37(3):120-130, China Pharmaceutical University, China (Mar. 2013).
Byrn, S.R., et al., "Solid-state Pharmaceutical Chemistry," Chem Mater 6:1148-1158, American Chemical Society, United States (1994).
Vippagunta, S.R., et al., "Crystalline solids," Advanced Drug Delivery Reviews 48:3-26, Elsevier, Netherlands (2001).

* cited by examiner

*Primary Examiner* — D Margaret M Seaman
(74) *Attorney, Agent, or Firm* — Sterne, Kessler, Goldstein & Fox P.L.L.C.

(57) ABSTRACT

Provided are a fruquintinib and a saccharin salt or eutectic crystal, a fruquintinib and a malonic acid eutectic crystal or a fruquintinib and a maleic eutectic crystal, a preparation method therefor, a pharmaceutical composition containing thereof, and uses thereof in preparing drugs for treating and/or preventing diseases related to abnormal angiogenesis, such as cancer, tumors, macular degeneration, chronic inflammation and the like.

29 Claims, 11 Drawing Sheets

FRUQUINTINIB EUTECTIC CRYSTAL, PREPARATION METHOD THEREFOR, COMPOSITION, AND USES THEREOF

FIELD OF THE INVENTION

The present invention relates to the technical field of crystallization in pharmaceutical chemistry. Specifically, the present invention relates to novel cocrystals of fruquintinib and the preparation methods and uses thereof, as well as the pharmaceutical compositions of the new crystalline forms.

BACKGROUND OF THE INVENTION

Fruquintinib is a novel oral small molecule drug, which can effectively inhibit the activity of vascular endothelial growth factor receptors (VEGFRs), thus inhibit the proliferation of vascular endothelial cells, formation of lumens, etc., and ultimately inhibit tumor growth by inhibiting tumor neovascularization. It is suitable for the treatment of cancers, tumors, macular lesions, chronic inflammatory diseases associated with abnormal angiogenesis in patients.

The chemical name of fruquintinib is 6-(6,7-dimethoxy-quinazoline-4-oxy)-N,2-dimethyl benzofuran-3-formamide and its chemical structural formula is as follows:

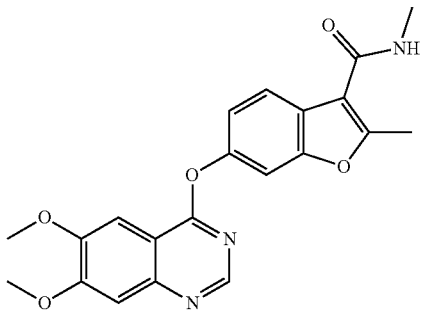

The patent WO2009137797A2 disclosed the compound of fruquintinib and its preparation methods, pharmaceutical compositions and the uses for treating the diseases related to abnormal angiogenesis.

The patent CN101575333B disclosed the compound of fruquintinib and its preparation methods and pharmaceutical compositions thereof, and mentioned their pharmaceutically acceptable salts and their uses for the treatment of the diseases associated with abnormal angiogenesis, but did not mention the crystalline forms, preparation methods and characterization data of the acceptable salts.

The patent CN105461702A disclosed six crystalline forms of fruquintinib compound, three anhydrous forms (Form I, Form III and Form VII), a hemi-ethanol solvate (Form II), a mono acetic acid solvate (Form IV), and a monodioxane solvate (Form VIII), respectively. It also disclosed the characterization data of their preparation methods and their X-ray powder diffraction patterns, differential scanning calorimetry (DSC) patterns and thermogravimetric (TGA) patterns.

The patent CN105777721A disclosed Form A of fruquintinib compound and the preparation methods and powder X-ray diffraction patterns thereof. This crystalline form is substantially consistent with the Form I in the patent CN105461702A.

The patent CN105777722A disclosed Form C of fruquintinib compound and the preparation methods and powder X-ray diffraction patterns thereof. This crystalline form is substantially consistent with the Form III in the patent CN105461702A.

The patent CN105777723A disclosed Form B of fruquintinib compound and the preparation methods and powder X-ray diffraction patterns thereof. This crystalline form is substantially consistent with the Form I in the patent CN105461702A.

During the study, the inventors of the present invention found that, among the known fruquintinib crystalline forms, Form I can be obtained constantly in various solvent systems and methods, and has high crystal stability. The inventors also found that particles of Form I are fine needle-shaped, and the fine needle-shaped particles are usually poor in flowability, difficult to be filtrated and dried, difficult to be mixed evenly with excipients, and thus affect the processability. In addition, Form I is hydrophobic and has poor solubility in water, affecting its dissolution and bioavailability.

The inventors also found that solvates such as mono acetic acid solvate are unstable, and cannot maintain the original crystalline form in water, and will transform into the known fruquintinib Form I.

According to the above patent documents, fruquintinib has nine crystalline forms. This phenomenon of polymorphism makes it difficult to obtain a pure crystalline form during crystallization process, which affects the process repeatability and the product quality, and easy to incorporate more impurities.

Therefore, according to the defects of the prior art, it is still necessary to develop new solid forms of fruquintinib compounds.

SUMMARY OF THE INVENTION

The purpose of the present invention is to provide novel compounds formed by fruquintinib and ion pairs and the crystalline forms, preparation methods and uses thereof as well as the pharmaceutical compositions containing fruquintinib compounds thereof. Compared with the known fruquintinib solid forms, the compounds of the present invention have one or more improved properties, especially in the aspects of higher water solubility, higher dissolution rate, better stability, better flowability and favorable processability, etc. Preferably, the new solid forms of the present invention have higher solubility and better particle morphology.

One aspect of the present invention is to provide the compound formed by fruquintinib and saccharin ("Compound A") and its crystalline form ("Crystalline Form of Compound A") and the preparation methods thereof.

The present invention provides Compound A containing fruquintinib and saccharin at a molar ratio of 1:1 and with the structural formula as follows:

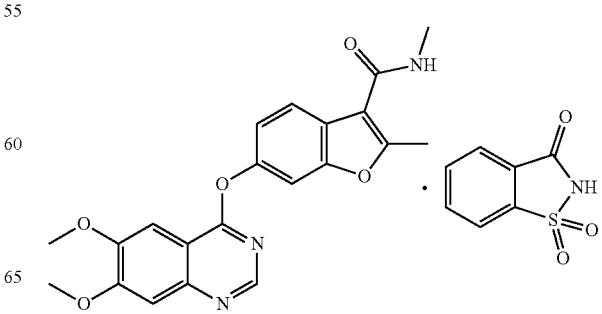

In a preferred embodiment of the present invention, Compound A is crystalline, preferably, non-solvent, hydrate and anhydrous, more preferably, anhydrous. In a further preferred embodiment of the present invention, the X-ray powder diffraction pattern of the Crystalline Form of Compound A, expressed as 2θ angles, has the following characteristic peaks: 5.0±0.2°, 13.2±0.2°, 15.4±0.2° and 17.0±0.2°.

More preferably, the X-ray powder diffraction pattern of the Crystalline Form of Compound A, expressed as 2θ angles, has the following characteristic peaks: 5.0±0.2°, 10.8±0.2°, 11.5±0.2°, 13.2±0.2°, 14.8±0.2°, 15.4±0.2°, 17.0±0.2°, 23.8±0.2° and 25.4±0.2°.

Further preferably, the X-ray powder diffraction pattern of the Crystalline Form of Compound A, expressed as 2θ angles, essentially has the following characteristic peaks and relative intensities:

| 2θ | Relative intensity % |
|---|---|
| 5.0 ± 0.2° | 100 |
| 9.8 ± 0.2° | 22.4 |
| 10.4 ± 0.2° | 20.1 |
| 10.8 ± 0.2° | 35.3 |
| 11.5 ± 0.2° | 37.9 |
| 12.5 ± 0.2° | 18.3 |
| 13.2 ± 0.2° | 54.3 |
| 13.7 ± 0.2° | 16 |
| 14.8 ± 0.2° | 31.7 |
| 15.4 ± 0.2° | 74 |
| 16.1 ± 0.2° | 26.3 |
| 17.0 ± 0.2° | 50.9 |
| 17.8 ± 0.2° | 21.2 |
| 18.3 ± 0.2° | 21.9 |
| 20.4 ± 0.2° | 34.4 |
| 20.8 ± 0.2° | 16.1 |
| 21.6 ± 0.2° | 19.2 |
| 22.1 ± 0.2° | 34.6 |
| 22.8 ± 0.2° | 33.6 |
| 23.1 ± 0.2° | 21.6 |
| 23.8 ± 0.2° | 86.9 |
| 25.1 ± 0.2° | 21 |
| 25.4 ± 0.2° | 74.2 |
| 26.4 ± 0.2° | 40.5 |
| 26.9 ± 0.2° | 27 |
| 27.8 ± 0.2° | 15.6 |
| 28.8 ± 0.2° | 19.2 |

Non-restrictively, in one typical embodiment, the X-ray powder diffraction (XRPD) pattern of the Crystalline Form of Compound A is substantially as shown in FIG. 4.

Non-restrictively, in one typical embodiment, the TGA pattern of the Crystalline Form of Compound A is substantially as shown in FIG. 5, which indicates that the Crystalline Form of Compound A is anhydrous.

Non-restrictively, in one typical embodiment, the DSC pattern of the Crystalline Form of Compound A is substantially as shown in FIG. 6, showing a melting point of 232° C.

Non-restrictively, in one specific embodiment, the IR pattern of the Crystalline Form of Compound A is substantially as shown in FIG. 7, which indicates that Crystalline Form of Compound A has characteristic peaks in the locations with wave number of 1650±2 $cm^{-1}$, 1507±2 $cm^{-1}$, 1422±2 $cm^{-1}$, 1395±2 $cm^{-1}$, 1371±2 $cm^{-1}$, 1274±2 $cm^{-1}$, 1252±2 $cm^{-2}$, 1226±2 $cm^{-1}$, 1145±2 $cm^{-1}$, 937±2 cm-1, 877±2 $cm^{-1}$ and 756±2 $cm^{-1}$.

Another purpose of the present invention is to provide the single crystal of the Crystalline Form of Compound A and the preparation methods thereof.

In one embodiment of the present invention, the single crystal of Compound A was prepared as follows: dissolving the Crystalline Form of Compound A in a mixed solvent of tetrahydrofuran and chloroform to form a solution, volatilizing the solution at 40° C. through a small hole to obtain the single crystal. "Volatilizing through a small hole" means that the solution is placed in a container and volatilizes for crystallization through a small hole with 1 to 2 mm in diameter at the corresponding temperature.

The single crystal of Compound A belongs to the triclinic system with space group P1, and, measured at 106K, has the following single crystal unit cell parameters: a=8.6 Å±0.2 Å, b=9.0 Å±0.2 Å, c=17.3 Å±0.2 Å; and dihedral angles: α=84.0°±0.2°, β=77.4°±0.2°, γ=77.8°±0.2°.

Preferably, the unit cell parameters of the single crystal of Compound A are: a=8.5 Å to 8.7 Å; b=8.9 Å to 9.1 Å; c=17.2 Å to 17.4 Å; α=83.9° to 84.1°; β=77.3° to 77.5° and γ=77.7° to 77.9°. More specifically, the unit cell parameters of the single crystal of the cocrystal are: a=8.61 Å to 8.62 Å; b=8.95 Å to 8.96 Å; c=17.31 Å to 17.32 Å; α=84.03° to 84.04°; β=77.36° to 77.37° and γ=77.77° to 77.78°.

In a specific embodiment, the unit cell parameters were: a=8.6146(10)Å, b=8.9574(11)Å and c=17.310(2)Å; and dihedral angles: α=84.030(10°), β=77.369(10°) and γ=77.771(10°).

Further, in a specific embodiment of the present invention, Compound A has the following atomic coordinates.

| Atom | X | Y | Z |
|---|---|---|---|
| S1 | 6100.9(8) | 419.7(7) | 2756.2(4) |
| O2 | 9429(2) | 3065(2) | 6171.2(11) |
| O6 | 6049(2) | −2480(2) | 4413.6(11) |
| O3 | 9537(2) | −2321(2) | 7420.0(11) |
| O1 | 8070(2) | 3208(2) | 4983.8(11) |
| O4 | 7059(2) | −5470(2) | 9582.4(12) |
| N2 | 8512(3) | −3534(2) | 6587.1(13) |
| O7 | 4897(2) | 1813(2) | 2760.3(12) |
| O8 | 7683(2) | 510(2) | 2275.2(11) |
| N1 | 7591(3) | −2099(2) | 5500.2(12) |
| O5 | 12063(3) | −8357(3) | 9779.7(14) |
| N3 | 10143(3) | −8958(3) | 10805.5(13) |
| C5 | 7746(3) | 570(3) | 5194.7(14) |
| C3 | 8703(3) | −862(3) | 6337.2(15) |
| N4 | 6269(3) | −248(3) | 3653.4(13) |
| C12 | 8130(3) | −3847(3) | 8451.1(16) |
| C1 | 7877(3) | −3388(3) | 5941.8(15) |
| C25 | 4948(3) | −1377(3) | 1802.5(17) |
| C4 | 8003(3) | −795(3) | 5671.4(15) |
| C6 | 8235(3) | 1827(3) | 5387.4(15) |
| C8 | 9198(3) | 429(3) | 6527.6(15) |
| C7 | 8983(3) | 1756(3) | 6062.6(15) |
| C23 | 5332(3) | −2188(3) | 3140.5(15) |
| C22 | 5908(3) | −1646(3) | 3795.1(15) |
| C11 | 9571(3) | −3603(3) | 7969.7(15) |
| C2 | 8884(3) | −2285(3) | 6779.5(14) |
| C14 | 9789(3) | −5924(3) | 9138.3(15) |
| C10 | 10097(3) | 3049(3) | 6863.5(16) |
| C16 | 11079(3) | −4444(3) | 8050.6(16) |
| C21 | 11280(4) | −10098(3) | 11164.3(16) |
| C28 | 4819(3) | −3542(3) | 3114.9(17) |
| C27 | 4359(3) | −3812(3) | 2427.7(18) |
| C13 | 8307(3) | −5027(3) | 9030.2(16) |
| C15 | 11205(3) | −5626(3) | 8636.2(16) |
| C9 | 7228(3) | 3394(3) | 4334.0(16) |
| C19 | 10631(3) | −8145(3) | 10138.9(16) |
| C17 | 9394(3) | −6970(3) | 9820.5(16) |
| C24 | 5383(3) | −1131(3) | 2493.8(16) |
| C26 | 4432(4) | −2749(4) | 1782.2(18) |
| C18 | 7767(4) | −6659(4) | 10055.7(18) |
| C20 | 6565(4) | −7323(5) | 10676(2) |
| O9 | 5056(11) | 675(10) | 156(5) |
| H1 | 7130 | −2082 | 5092 |
| H3 | 9108 | −8797 | 11032 |
| H5 | 7247 | 623 | 4752 |
| H12 | 7104 | −3257 | 8390 |

-continued

| Atom | X | Y | Z |
|---|---|---|---|
| H1A | 7610 | −4273 | 5786 |
| H25 | 4997 | −649 | 1362 |
| H8 | 9678 | 380 | 6977 |
| H10A | 9236 | 3042 | 7339 |
| H10B | 10567 | 3962 | 6838 |
| H10C | 10942 | 2131 | 6886 |
| H16 | 12029 | −4213 | 7705 |
| H21A | 12120 | −10619 | 10747 |
| H21B | 10704 | −10848 | 11494 |
| H21C | 11785 | −9600 | 11495 |
| H28 | 4782 | −4270 | 3556 |
| H27 | 3992 | −4729 | 2400 |
| H15 | 12234 | −6216 | 8692 |
| H9A | 6132 | 3190 | 4530 |
| H9B | 7821 | 2675 | 3931 |
| H9C | 7160 | 4444 | 4100 |
| H26 | 4125 | −2960 | 1316 |
| H20A | 6477 | −6889 | 11184 |
| H20B | 6921 | −8436 | 10728 |
| H20C | 5505 | −7081 | 10523 |

Non-restrictively, in one typical embodiment, the PLM of the single crystal of Compound A is substantially as shown in FIG. 8, indicating block like crystals.

Non-restrictively, in one typical embodiment, the $^1$H NMR spectrum of Compound A is substantially as shown in FIG. 9, which indicates that the ratio of fruquintinib to saccharin is 1:1.

The present invention is to provide the preparation methods for Compound A, comprising directly reacting fruquintinib with 0.67 to 3 equivalents of saccharin, preferably, an acid base reaction in an organic solvent or a solvent combination. The organic solvent is a solvent that can dissolve fruquintinib or saccharin.

The preparation methods of the Crystalline Form of Compound A of the present invention comprise any one of the following preparation methods:

1) mixing fruquintinib and saccharin at a molar ratio of 1:0.67 to 1:1.5 for reaction in a solvent selected from the group consisting of an alcohol, an ester, a haloalkane, an ether (including cycloether), a ketone, acetonitrile, and any mixture thereof; removing the solvent to obtain the Crystalline Form of Compound A;

preferably, the solvent is selected from the group consisting of chloroform, methanol, ether, ethyl acetate, acetone, and any mixture thereof;

preferably, the molar ratio of fruquintinib and saccharin is 1:1 to 1:1.5.

preferably, the operation temperature is 10 to 50° C., more preferably, room temperature;

preferably, the crystallization time is 8 to 48 hours, more preferably 8 to 24 hours;

preferably, the mass-to-volume ratio of fruquintinib and solvent is 5 to 50 mg:1 ml;

preferably, the mass-to-volume ratio of saccharin and the solvent is 2 to 20 mg:1 ml.

2) adding a solvent to the mixture of equal molar ratio of fruquintinib and saccharin, wetting the mixture completely by the solvent; grinding the solution until dry to obtain the Crystalline Form of Compound A, wherein, the solvent is selected from the group consisting of water, an alcohol, an ester, an alkane (including haloalkane), an ether (including cycloether), a ketone, acetonitrile, and any mixture thereof;

preferably, the solvent is selected from the group consisting of acetone, methanol, tetrahydrofuran, water, acetonitrile, and any mixture thereof;

preferably, the weight-to-volume ratio of the mixture to the solvent is 20 to 220 mg:1 ml;

preferably, the operation temperature of the preparation method is 10 to 40° C., more preferably, room temperature.

3) adding the mixture of equal molar of fruquintinib and saccharin to the mixed organic solvents to form a solution, wherein, the organic solvent is selected from the group consisting of an alcohol, an ether (including cycloether), an ester, a haloalkane, a ketone, acetonitrile, nitromethane, and any mixture thereof, volatilizing naturally to obtain Compound A Crystalline Form;

preferably, the organic solvent is selected from the group consisting of methanol, dichloromethane, tetrahydrofuran, acetone, acetonitrile, nitromethane, and any mixture thereof;

preferably, the operation temperature of the preparation method is 10 to 50° C., more preferably, room temperature;

preferably, the weight-to-volume ratio of the mixture to the solvent is 5 to 50 mg:1 ml.

Compound A and its crystalline form have the following unexpected beneficial effects:

Comparative Example 1 shows that the Crystalline Form of Compound A in the present invention has a higher solubility in 25° C. water than that of the known fruquintinib Form I, indicating that the Crystalline Form of Compound A of the present invention has better solubility and thus may have better bioavailability.

The PLM shows that the known fruquintinib Form I particles are fine needle-shaped while the Crystalline Form of Compound A of the present invention has better particle morphology and is of block crystalline particles and thus has better flowability, which can reduce filtration time and sifting time and improve efficiency, and has better processability.

Having been placed in desiccators at room temperature and RH 10% to 90% for 4 months, the Crystalline Form of Compound A of the present invention is kept its appearance, XRPD and melting point all unchanged, indicating that the Crystalline Form of Compound A of the present invention has good storage stability, avoiding or reducing the quality, safety and stability related problems, such as content uniformity and impurity issues during drug manufacturing and/or storage of the active ingredient and the formulations containing the Crystalline Form of Compound A and also avoid special and expensive packaging.

Comparative Example 2 shows that the Crystalline Form of Compound A of the present invention kept its form unchanged after having been stirred in water for 24 hours while the crystalline form of the known fruquintinib mono acetic acid solvate changed, indicating that the Crystalline Form of Compound A of the present invention has better crystal stability.

The second aspect of the present invention is to provide a cocrystal formed by fruquintinib and malonic acid and its crystalline form and the preparation methods thereof.

The present invention provides a cocrystal of fruquintinib and malonic acid at a molar ratio of 1:1 and with the structural formula as follows:

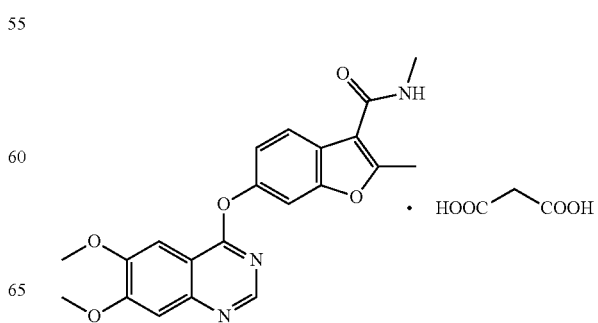

In a preferred embodiment of the present invention, the X-ray powder diffraction pattern of the crystalline form of the cocrystal of fruquintinib and malonic acid, expressed as 2θ angles, has the following characteristic peaks: 10.9±0.2°, 14.2±0.2°, 16.4±0.2° and 19.9±0.2°.

More preferably, the X-ray powder diffraction pattern of the crystalline form of the cocrystal of fruquintinib and malonic acid, expressed as 2θ angles, has the following characteristic peaks: 9.8±0.2°, 10.9±0.2°, 11.6±0.2°, 14.2±0.2°, 14.9±0.2°, 16.4±0.2° and 19.9±0.2°.

Further preferably, the X-ray powder diffraction pattern of the crystalline form of the cocrystal of fruquintinib and malonic acid, expressed as 2θ angles, has the following characteristic peaks and relative intensities:

| 2θ | Relative intensity % |
|---|---|
| 5.3 ± 0.2° | 13.0 |
| 5.7 ± 0.2° | 37.3 |
| 9.8 ± 0.2° | 56.7 |
| 10.9 ± 0.2° | 100.0 |
| 11.6 ± 0.2° | 49.9 |
| 14.2 ± 0.2° | 62.0 |
| 14.9 ± 0.2° | 18.8 |
| 15.3 ± 0.2° | 29.6 |
| 16.4 ± 0.2° | 69.3 |
| 19.9 ± 0.2° | 71.7 |
| 22.1 ± 0.2° | 11.4 |
| 23.5 ± 0.2° | 10.3 |
| 25.0 ± 0.2° | 20.6 |
| 33.1 ± 0.2° | 10.6 |
| 37.8 ± 0.2° | 10.3 |

Non-restrictively, in one typical embodiment, the X-ray powder diffraction pattern (XRPD) of the crystalline form of the cocrystal of fruquintinib and malonic acid is substantially as shown in FIG. 10.

Non-restrictively, in one typical embodiment, the TGA thermogram of the crystalline form of the cocrystal of fruquintinib and malonic acid is substantially as shown in FIG. 11, indicating that the crystalline form of the cocrystal is anhydrous.

Non-restrictively, in one typical embodiment, the DSC thermogram of the crystalline form of the cocrystal of fruquintinib and malonic acid is substantially as shown in FIG. 12, which indicates that the crystalline form of the cocrystal has a melting point of 138° C.

Non-restrictively, in one typical embodiment, the IR spectrum of the crystalline form of the cocrystal of fruquintinib and malonic acid is substantially as shown in FIG. 13, which indicates that the crystalline form of the cocrystal has characteristic peaks in wave number of 1741±2 $cm^{-1}$, 1663±2 $cm^{-1}$, 1609±2 $cm^{-1}$, 1509±2 $cm^{-1}$, 1421±2 $cm^{-1}$, 1390±2 $cm^{-1}$, 1227±2 $cm^{-1}$, 1122±2 $cm^{-1}$, 983±2 $cm^{-1}$, 838±2 $cm^{-1}$ and 738±2 $cm^{-1}$.

Non-restrictively, in one typical embodiment, the PLM of the crystalline form of the cocrystal of fruquintinib and malonic acid is substantially as shown in FIG. 14, showing block crystals.

Non-restrictively, in one typical embodiment, the $^1$HNMR spectrum of the crystalline form of the cocrystal of fruquintinib and malonic acid is substantially as shown in FIG. 15, which indicates that the ratio of fruquintinib to malonic acid is 1:1.

The present invention is to provide the preparation methods for the cocrystal of fruquintinib and malonic acid, comprising directly reacting fruquintinib with 0.5 to 2.5 equivalents of malonic acid, preferably, an acid base reaction is in an organic solvent or solvent combination. The organic solvent is a solvent that can dissolve fruquintinib or malonic acid. The present invention provides the preparation methods of the crystalline form of the cocrystal of fruquintinib and malonic acid, comprising any of the following preparation methods:

1) mixing fruquintinib and malonic acid at a molar ratio of 1:0.5 to 1:2 in a solvent selected from an alcohol, a haloalkane, an ether (including cycloether), a ketone, acetonitrile, and any mixture thereof, for reaction; removing the solvent to obtain the crystalline form of the cocrystal;

preferably, the solvent is selected from methanol, tetrahydrofuran, acetone, acetonitrile, and any mixture thereof;

preferably, the molar ratio of the fruquintinib to malonic acid is 1:0.5 to 1:1;

preferably, the operation temperature of the preparation method is 10 to 50° C., more preferably, room temperature;

preferably, the crystallization time is 8 to 48 hours, more preferably, 8 to 24 hours;

preferably, the mass-to-volume ratio of the fruquintinib to the solvent is 5 to 50 mg:1 ml.

preferably, the mass-to-volume ratio of the malonic acid to the solvent is 1 to 30 mg: 1 ml.

2) adding a solvent to the equal molar ratio mixture of fruquintinib and malonic acid, completely wetting the mixture, and grinding it until dry to obtain the crystalline form of the cocrystal of fruquintinib and malonic acid, wherein, the solvent is selected from the group consisting of water, an alcohol, an ester, an alkane (including haloalkane), an ether (including cycloether), a ketone, acetonitrile, and any mixture thereof;

preferably, the solvent is selected from acetonitrile, methanol, water, and any mixture thereof;

preferably, the weight-to-volume ratio of the mixture to the solvent is 20 to 253 mg:1 ml;

preferably, the operation temperature of the preparation method is 10 to 40° C., more preferably, room temperature.

3) Forming a solution of a mixture of equal molar ratio of fruquintinib and malonic acid in a mixed organic solvent to form a solution (wherein, the organic solvents are selected from the group consisting of an alcohol, an ether (including cycloether), a haloalkane, a ketone, acetonitrile, and any mixture thereof), volatilizing naturally to obtain the crystalline form of the cocrystal;

preferably, the organic solvent is selected from the group consisting of methanol, dichloromethane, chloroform, acetone, and any mixture thereof;

preferably, the operation temperature of the preparation method is 10 to 50° C., more preferably, room temperature;

preferably, the weight-to-volume ratio of the mixture to the solvent is 1 to 50 mg:1 ml;

The cocrystal of fruquintinib and malonic acid have the following beneficial effects:

Comparative Example 1 shows that the cocrystal of fruquintinib and malonic acid of the present invention has a higher solubility at 25° C. in water than that of the known fruquintinib Form I, indicating that the cocrystal of fruquintinib and malonic acid of the present invention has better solubility and thus may have better bioavailability.

The PLM shows that the known fruquintinib Form I particles are fine needle-shaped while the cocrystal of fruquintinib and malonic acid of the present invention has better particle morphology and is block crystals and has better flowability, which can reduce filtration time and sifting time of API and improve efficiency, and has better processability.

Having been placed in desiccators at room temperature and RH 10% to 90% for 4 months, cocrystal of fruquintinib and malonic acid of the present invention is kept its appearance, XRPD and melting point all unchanged, indicating that the cocrystal of fruquintinib and malonic acid of the present invention has good storage stability, avoiding or reducing the quality, safety and stability related problems, such as content uniformity and impurity issues during drug manufacturing and/or storage of the active ingredient and the formulations containing the cocrystal of fruquintinib and malonic acid and also avoid special and expensive packaging.

Comparative Example 2 shows that the crystalline form of the cocrystal of fruquintinib and malonic acid of the present invention kept its form unchanged after having been stirred in water for 24 hours while the crystalline form of the known fruquintinib monoacetate changes, indicating that the crystalline form of the cocrystal of fruquintinib and malonic acid of the present invention has better crystal stability.

The third aspect of the present invention is to provide a cocrystal formed by fruquintinib and maleic acid and its crystalline form and the preparation methods thereof.

The present invention provides the cocrystal of fruquintinib and maleic acid at a molar ratio of 1:1 and with the structural formula as follows:

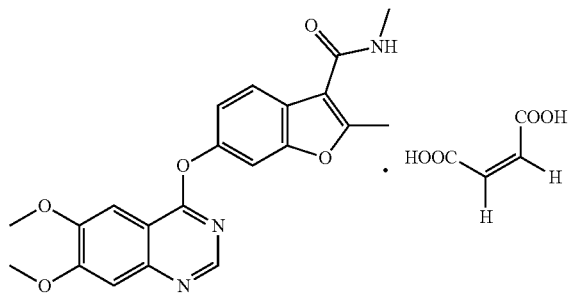

In a preferred embodiment of the present invention, the X-ray powder diffraction pattern of the crystalline form of the cocrystal of fruquintinib and maleic acid, expressed as 2θ angles, has the following characteristic peaks: 3.9±0.2°, 5.6±0.2°, 8.9±0.2° and 15.0±0.2°.

More preferably, the X-ray powder diffraction pattern of the crystalline form of the cocrystal of fruquintinib and maleic acid, expressed as 2θ angles, has the following characteristic peaks: 8.4±0.2°, 11.4±0.2°, 17.6±0.2°, 23.4±0.2° and 27.4±0.2°.

Further preferably, the X-ray powder diffraction pattern of the crystalline form of the cocrystal of fruquintinib and maleic acid, expressed as 2θ angles, has the following characteristic peaks and relative intensities:

| 2θ | Relative intensity % |
|---|---|
| 3.9 ± 0.2° | 20.9 |
| 5.6 ± 0.2° | 100.0 |
| 7.6 ± 0.2° | 13.8 |
| 8.4 ± 0.2° | 26.9 |
| 8.9 ± 0.2° | 55.6 |
| 10.8 ± 0.2° | 12.3 |
| 11.4 ± 0.2° | 27.7 |
| 12.7 ± 0.2° | 20.5 |
| 15.0 ± 0.2° | 60.3 |
| 16.2 ± 0.2° | 24.3 |
| 17.6 ± 0.2° | 29.7 |
| 23.4 ± 0.2° | 23.8 |
| 24.2 ± 0.2° | 26.5 |
| 24.9 ± 0.2° | 16.6 |
| 26.4 ± 0.2° | 23.4 |
| 27.4 ± 0.2° | 33.2 |
| 28.9 ± 0.2° | 14.5 |

Non-restrictively, in one typical embodiment, the X-ray powder diffraction pattern of the crystalline form of the cocrystal of fruquintinib and maleic acid is substantially as shown in FIG. 16.

Non-restrictively, in one typical embodiment, the TGA thermogram of the crystalline form of the cocrystal of fruquintinib and maleic acid is substantially as shown in FIG. 17, which indicates that the crystalline form of the cocrystal of fruquintinib and maleic acid is anhydrous.

Non-restrictively, in one typical embodiment, the DSC thermogram of the crystalline form of the cocrystal of fruquintinib and maleic acid is substantially as shown in FIG. 18, which indicates that the crystalline form of the cocrystal has a melting point of 157° C.

Non-restrictively, in one typical embodiment, the IR spectrum of the crystalline form of the cocrystal of fruquintinib and maleic acid is substantially as shown in FIG. 19, which indicates that the crystalline form of the cocrystal of fruquintinib and maleic acid has characteristic peaks at wave number of 1627±2 $cm^{-1}$, 1510±2 $cm^{-1}$, 1422±2 $cm^{-1}$, 1398±2 $cm^{-1}$, 1233±2 $cm^{-1}$, 1126±2 $cm^{-1}$, 986±2 $cm^{-1}$, 861±2 $cm^{-1}$ and 650±2 $cm^{-1}$.

Non-restrictively, in one typical embodiment, the PLM of the crystalline form of the cocrystal of fruquintinib and maleic acid is substantially as shown in FIG. 20, which indicates that the crystalline form of the cocrystal is block crystals.

Non-restrictively, in one typical embodiment, the $^{1}$HNMR spectrum of the crystalline form of the cocrystal is substantially as shown in FIG. 21, which indicates that the ratio of fruquintinib to maleic acid is 1:1.

The present invention is to provide the preparation methods for the cocrystal of fruquintinib and maleic acid, comprising directly reacting fruquintinib with 0.5 to 3 mole equivalents of maleic acid, preferably, an acid base reaction in an organic solvent or solvent combination. The organic solvent is a solvent that can dissolve fruquintinib or maleic acid.

The present invention provides the preparation methods of the crystalline form of the cocrystal of fruquintinib and maleic acid, comprising any of the following methods:

1) mixing fruquintinib and maleic acid at a molar ratio of 1:0.5 to 1:1.5 in a solvent selected from the group consisting of an alcohol, a haloalkane, a ketone, an acetonitrile, and any mixture thereof, for reaction; removing the solvent to obtain the crystalline form of the cocrystal;

preferably, the solvent is selected from the group consisting of methanol, dichloromethane, acetone, acetonitrile, and any mixture thereof;

preferably, the molar ratio of the fruquintinib to maleic acid is 1:0.5 to 1:1;

preferably, the operation temperature of the preparation method is 10 to 50° C., more preferably room temperature;

preferably, the crystallization time is 8 to 48 hours, more preferably, 8 to 24 hours;

preferably, the mass-to-volume ratio of the fruquintinib to the solvent is 5 to 50 mg:1 ml.

preferably, the mass-to-volume ratio of the maleic acid to the solvent is 3 to 20 mg:1 ml.

2) adding a solvent to the mixture of equal molar ratio of fruquintinib and maleic acid, completely wetting the mixture and grinding it until dry to obtain the crystalline form of the cocrystal, wherein, the solvent is selected from the group consisting of water, an alcohol, an ester, an alkane, an ether (including cycloether), a ketone, acetonitrile, and any mixture thereof;

preferably, the solvent is selected from the group consisting of isopropanol, methanol, acetone, water, acetonitrile, and any mixture thereof;

preferably, the weight-to-volume ratio of the mixture to the solvent is 20 to 205 mg:1 ml;

preferably, the operation temperature of the preparation method is 10 to 50° C., more preferably, room temperature.

3) Forming a solution of a mixture of equal molar ratio of fruquintinib and maleic acid in a mixed organic solvent to form a solution, wherein, the organic solvents is selected from an alcohol, a ketone, a cycloether, a haloalkane, acetonitrile, and any mixture thereof, volatilizing naturally to obtain the crystalline form of the cocrystal of fruquintinib and maleic acid;

preferably, the organic solvent is selected from methanol, dichloromethane, chloroform, acetone, and any mixture thereof;

preferably, the operation temperature of the preparation method is 10 to 50° C., more preferably, room temperature;

preferably, the weight-to-volume ratio of the mixture to the solvent is 1 to 50 mg:1 ml.

The cocrystal of fruquintinib and maleic acid have the following beneficial effects:

Comparative Example 1 shows that the crystalline form of the cocrystal of fruquintinib and maleic acid of the present invention has a higher solubility at 25° C. in water than that of the known fruquintinib Form I, indicating that the crystalline form of the cocrystal of fruquintinib and maleic acid of the present invention has better solubility and thus may have better bioavailability.

The PLM shows that the known fruquintinib Form I particles are fine needle-shaped while the crystalline form of the cocrystal of fruquintinib and maleic acid of the present invention has better particle morphology and is of block shaped particles and has better flowability, which can reduce filtration time and sifting time of API and improve efficiency, and has better processability.

Having been placed in desiccators at room temperature and RH 10% to 90% for 4 months, the crystalline form of the cocrystal of fruquintinib and maleic acid of the present invention is kept its appearance, XRPD and melting point all unchanged, indicating that the crystalline form of the cocrystal of fruquintinib and malonic acid of the present invention has good storage stability, avoiding or reducing the quality, safety and stability related problems, such as content uniformity and impurity issues during drug manufacturing and/or storage of the active ingredient and the formulations containing the crystalline form of the cocrystal of fruquintinib and maleic acid and also avoid special and expensive packaging.

Comparative Example 2 shows that the crystalline form of the cocrystal of fruquintinib and maleic acid of the present invention kept its form unchanged after having been stirred in water for 24 hours while the crystalline form of the known fruquintinib mono acetic acid solvate compound changes, indicating that the crystalline form of the cocrystal of fruquintinib and maleic acid of the present invention has better crystal stability.

In any preparation method of Compound A, cocrystal of fruquintinib and malonic acid, cocrystal of fruquintinib and maleic acid and the crystalline forms thereof:

Unless otherwise specified, the term "room temperature" refers to a temperature between 10° C. and 30° C.

The "cycloether" can be tetrahydrofuran, 1,4-dioxane, etc.

The "haloalkane" can be dichloromethane, chloroform, etc.

The "stirring" can be carried out by a conventional stirring method in the art, such as magnetic stirring, mechanical stirring and the stirring speed is 50 to 1,800 rpm, preferably 300 to 900 rpm.

The "separation" can be performed using conventional methods in the field, such as centrifugation or filtration. The preferred method is vacuum filtration, generally at a pressure less than atmosphere pressure at room temperature, preferably less than 0.09 Mpa. The "centrifugation" is to place the sample to be separated in a centrifuge tube, and centrifugate for example at 6,000 rpm, until the solid is all sunk to the bottom of the centrifuge tube.

The "drying" can be performed by routine methods in the field, such as room temperature drying, forced air drying or vacuum drying. Drying is performed under reduced pressure or atmospheric pressure, preferably less than 0.09 Mpa. Drying instruments and methods are unrestricted, and may be fume hood, blast oven, spray drying, fluidized bed drying or vacuum oven.

In the present invention, "crystal" or "crystalline form" refers to that characterized by X-ray powder diffraction pattern, having a unique ordered molecular arrangement or configuration within the crystalline unit cell. It is known to those skilled in the field that the experimental error depends on instrumental conditions, sample preparation and sample purity. The 2θ angles of the peaks in the XRPD pattern may change with the change of instruments and samples. The difference of peak locations may vary by 1°, 0.8°, 0.5°, 0.3°, 0.1°, etc. depending on the instruments and samples, and ±0.2° is usually allowed. The relative intensity of peaks may change with the change of sample, sample preparation, and other experimental conditions. Therefore, the order of peak intensities should not be regarded as the only or the determining factor. Due to the effect of experimental factors including sample height, the angles of peaks may shift overall. Hence, it is easily understood for those skilled in the field that any crystalline form having the same or similar X-ray powder diffraction pattern as that of the crystalline form in the present invention should be within the scope of the present invention. "pure crystalline form" or "single crystalline form" refer to a crystalline form confirmed by X-ray powder diffraction as a single form.

The crystalline forms the fruquintinib compound or cocrystal containing fruquintinib in the present invention are substantially pure, single, and substantially free of any other crystalline or amorphous form. As used herein, "substantially pure" when used in reference to a new crystalline form means that the new crystalline form comprises at least 80% (by weight) of the present compound, more preferably at least 95% (by weight), especially at least 95% (by weight), especially at least 99% (by weight).

The starting material "fruquintinib" can be obtained by referring to the method described in Embodiment 16 of patent document CN101575333B or commercially available. This patent document is incorporated into this application by reference in its entirety.

The fourth aspect of the present invention is to provide a pharmaceutical composition, which comprises the crystalline form of the compound containing fruquintinib or cocrystal of fruquintinib and at least one pharmaceutically acceptable excipient.

Further, the pharmaceutical composition comprises a therapeutically and/or preventively effective amount of one or more of the crystalline forms of the compound containing fruquintinib of the present invention or the crystalline forms of the compound containing fruquintinib prepared with the preparation methods of the present invention, and at least one pharmaceutically acceptable carrier or excipient. Wherein the crystalline forms of compound containing fruquintinib of the present invention include Compound A, the cocrystal of fruquintinib and malonic acid, and the cocrystal of fruquintinib and maleic acid. In addition, the pharmaceutical composition can also comprise other pharmaceutical compounds containing fruquintinib. Other pharmaceutically acceptable ionic pairs also includes benzoic acid, succinic acid, fumaric acid, citric acid, malic acid, tartaric acid, adipic acid, p-aminobenzoic acid, fructose, aspartame, benzyl alcohol, sorbitol, dextrin, maltodextrin, nicotinamide, urea and 2-aminopyrimidine.

According to the purpose of the present invention, the present invention is to provide a pharmaceutical composition, which comprises a therapeutically and/or preventively effective amount of one or more Compound A, the cocrystal of fruquintinib and malonic acid, and the cocrystal of fruquintinib and maleic acid or the above compounds prepared with the preparation methods of the present invention, and at least one pharmaceutically acceptable carrier or excipient. The content of the cocrystal in the pharmaceutical composition is, for example, 0.0001-50 wt %; preferably, 0.001-30 wt %; more preferably, 0.01-20 wt %. In addition, the pharmaceutical composition may also comprise one or more of other pharmaceutical crystalline forms and amorphous forms of pharmaceutical active ingredients, such as the cocrystal, pharmaceutical salt, solvate, crystalline or non-crystalline hydrate of fruquintinib.

The pharmaceutical composition can be made in solid, semi-solid or liquid dosage form or solid oral dosage form such as tablet, capsule, granule, pill and powder; or liquid oral dosage form such as solution, syrup, suspension, dispersant and emulsion; or injectable preparation, such as solution, dispersant, and lyophilized powder mixed into a solution. The formula can be suitable for rapid release, slow release or controlled release of active pharmaceutical ingredients, and can be conventional, dispersible, chewable, orally dissolved or rapidly melted preparations. The routes of administration include oral administration, intravenous injection, subcutaneous injection, transdermal administration, rectal administration and nasal administration. In order to maintain the co-crystal of the present invention during preparation, the pharmaceutical composition in the present invention preferably is the solid oral dosage forms, including tablets, capsules, granules, pills and powders; more preferably, sustained or controlled release solid oral dosage forms.

In a solid dosage form, the pharmaceutically acceptable carriers or auxiliaries of the present invention include, but are not limited to: diluent, such as starch, pregelatinized starch, lactose, powdered cellulose, microcrystalline cellulose, calcium hydrogen phosphate, tricalcium phosphate, mannitol, sorbitol, sugar, etc.; binder, such as gumArabic, guar gum, gelatin, polyvinylpyrrolidone, hydroxypropyl cellulose, hydroxypropyl methyl cellulose, polyethylene glycol, etc.; disintegrant, such as starch, sodium hydroxyacetate, pregelatinized starch, crosslinkedvidone, sodium acycarboxymethyl cellulose, colloidal silica, etc.; lubricant, such as stearic acid, magnesium stearate, zinc stearate, sodium benzoate, sodium acetate, etc.; flow aid, such as colloidal silica, etc.; complex forming agent, such as cyclodextrin or resin of various grades; release speed control agent, such as hydroxypropyl cellulose, carboxymethylcellulose, hydroxypropyl methyl cellulose, ethyl cellulose, methylcellulose, methyl methacrylate, wax, etc. Other pharmaceutically acceptable carriers or excipients available include, but are not limited to, film-forming agent, plasticizer, colorant, flavoring agent, viscosity regulator, preservative, and antioxidant.

The pharmaceutical composition can be prepared by methods commonly known to those skilled in the art. For example, the pharmaceutical composition can be prepared by blending Compound A, or the cocrystal of fruquintinib and malonic acid, or the cocrystal of fruquintinib and maleic acid of the present invention with one or more pharmaceutically acceptable carrier or auxiliary, optionally with one or more other pharmaceutically active ingredients. The solid dosage form can be prepared by direct blend and granulation process.

The fifth aspect of the present invention is to provide a use of the crystalline forms of the compound containing fruquintinib or the cocrystal of fruquintinib for in the preparation of medicines for treating and/or preventing the diseases associated with abnormal angiogenesis in patients, including age-related vascular degenerative lesions, such as cancer, tumor, age-related macular degeneration, chronic inflammatory diseases, etc. The cancer includes, but is not limited to, lung cancer, head and neck cancer, colorectal cancer, pancreatic cancer, colon cancer, breast cancer, ovarian cancer, prostate cancer, gastric cancer, renal cancer, liver cancer, brain cancer, bone cancer and sarcoma such as soft tissue sarcoma and leukemia. Further, the present invention is to provide a use of one or more compounds containing fruquintinib of the present invention or the compounds containing fruquintinib prepared with the preparation methods of the present invention in the preparation of medicines for treating and/or preventing the diseases associated with abnormal angiogenesis in patients. The compounds containing fruquintinib include Compound A, the cocrystal of fruquintinib and malonic acid and the cocrystal of fruquintinib and maleic acid.

Further, the present invention is to provide a method treating and/or preventing the diseases associated with abnormal angiogenesis in patients, comprising giving the patents in need a therapeutically and/or preventively effective amount of compound containing fruquintinib or the cocrystal of the fruquintinib of the present invention or its combination or pharmaceutical composition. The compounds containing fruquintinib include Compound A, the cocrystal of fruquintinib and malonic acid and the cocrystal of fruquintinib and maleic acid. The patients include but not are limited to mammal patients, such as human patients.

SPECIFIC IMPLEMENTATIONS

The following examples help to further understand the present invention, but are not intended to limit the contents of the present invention.

Testing Instruments and Methods:

X-ray powder diffraction (XRPD): performed on Bruker D8 Advance diffractometer. Samples were tested at room temperature. Testing conditions: 2θ scan range 3 to 40°, step size 0.02° and speed 0.2 s/step.

Polarized light microscopy (PLM) pictures were obtained from XP-500 Epolarized light microscope (by Shanghai Changfang Optical Instrument Co., LTD.) with 4× or 10× objective lens and 10× eyepiece, which was used to observe and photograph the morphology of samples.

Thermogravimetric (TGA) analysis data were collected on TA Instruments Q500 TGA. Method: segmented high resolution testing method that a sample was heated at a heating rate of 10° C./min under the protection of dry nitrogen ($N_2$).

Differential scanning calorimetry (DSC) analysis data were collected on TA Instruments Q200 DSC. Method: A sample was placed in a sealed aluminum pan and was heated at a heating rate of 10° C./min under the protection of dry nitrogen ($N_2$).

$^1$H nuclear magnetic resonance ($^1$H-NMR) data were collected on Bruker Avance II DMX 500 MHZ nuclear magnetic resonance spectrometer and a sample was dissolved with deuterium reagent.

Infrared (IR) analysis data were collected on Bruker Tensor 27 with OPUS software. Generally, data are collected within 600 to 4,000 $cm^{-1}$ by ATR means.

High performance liquid chromatography (HPLC) data were collected on Ultimate 3000 and the concentration was tested with the external standard method.

Unless particularly specified, embodiments were operated at room temperature and the solvent ratio was volume ratio.

Unless particularly specified, all reagents used in the embodiments were commercially available.

Ultrasonic operation in the embodiments could promote sample dissolution, and was performed with ultrasonic cleaner for 15 min at 40 kHz power.

Preparation Example 1

Fruquintinib was prepared by referring to the method of Example 1 in the patent CN101575333B.

Figure 1:
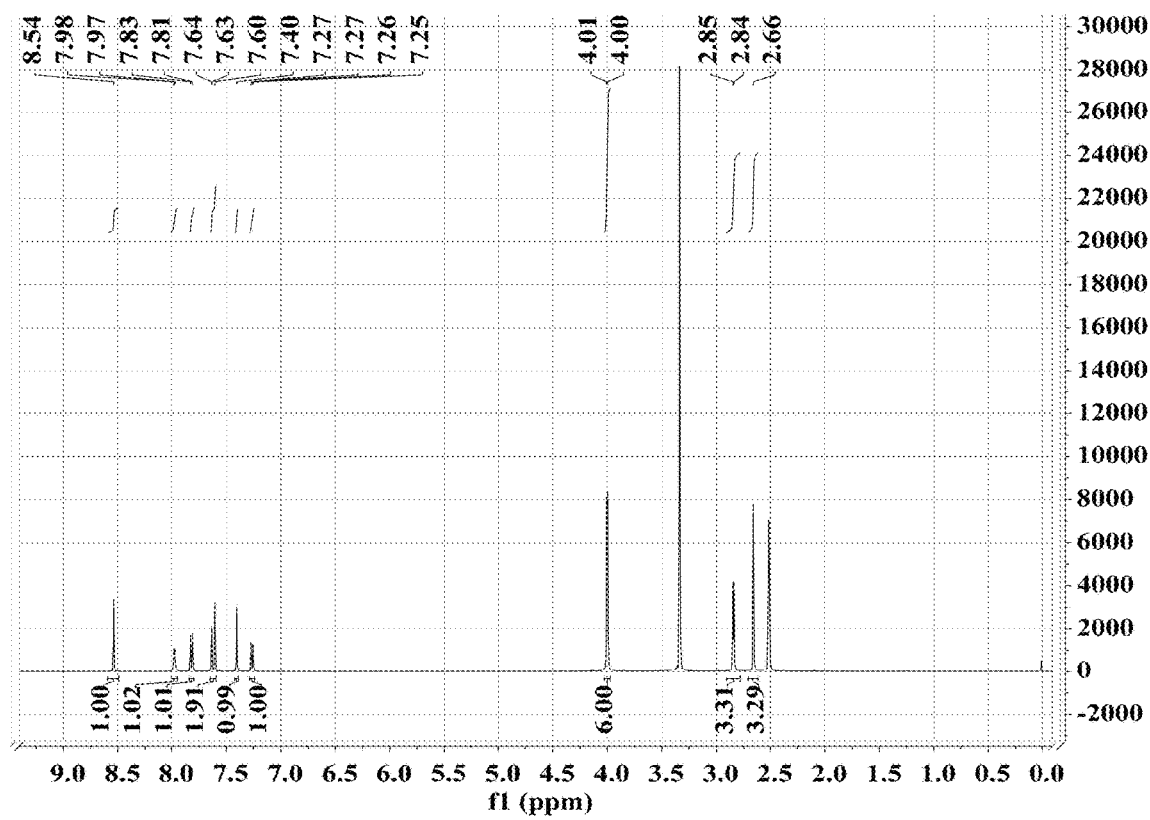
FIG. 1 is the $^1$HNMR spectrum of the known fruquintinib prepared with the method in Example 1 of the patent CN101575333B.

The $^1$HNMR spectrum is shown in FIG. 1, indicating that the fruquintinib is consistent with that prepared by referring to the method in Example 1 of the patent CN101575333B.

Preparation Example 2

Fruquintinib Crystalline Form I was prepared by referring to the method of Example 1 in the patent CN105461702 Å.

Figure 2:
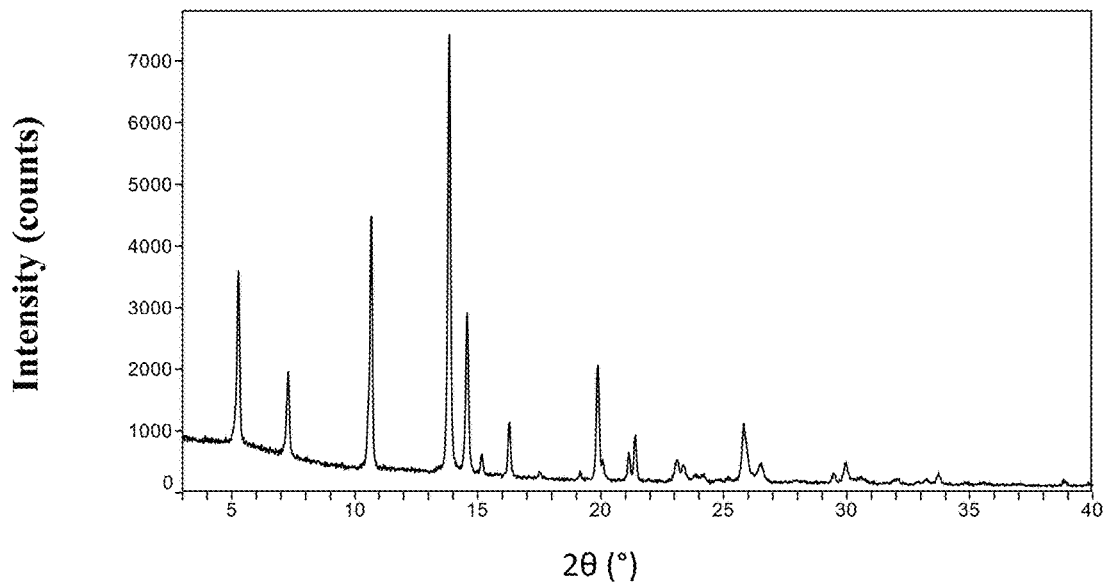
FIG. 2 is the XRPD pattern of the known fruquintinib prepared with the method in Example 1 of the patent CN105461702 Å.

Its XRPD pattern is shown in FIG. 2, indicating that the fruquintinib Crystalline Form I is consistent with that prepared by referring to the method in Example 1 of the patent CN105461702 Å.

Figure 3:
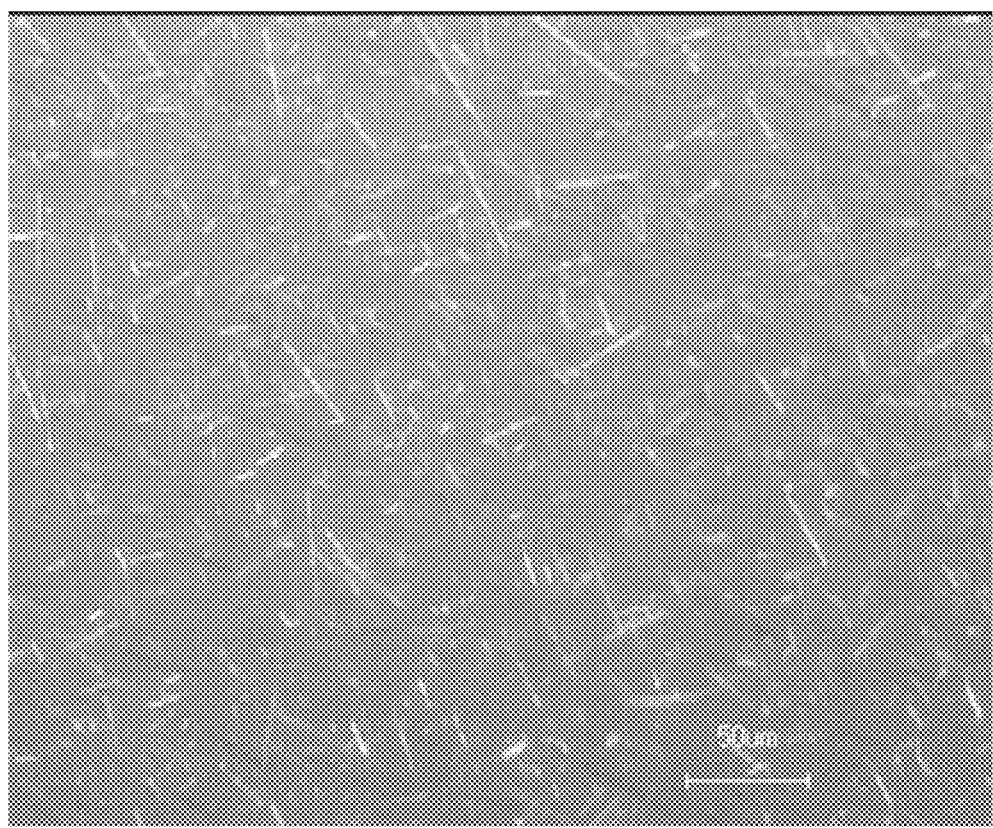
FIG. 3 is the PLM of the known fruquintinib prepared with the method in Example 1 of the patent CN105461702 Å.

Its PLM is shown in FIG. 3, indicating that fruquintinib Crystalline Form I is in fine needle shape.

Fruquintinib Crystalline Form III, fruquintinib mono acetic acid solvate (Crystalline Form IV) and Crystalline Form VII were prepared by referring to the methods of Example 34, Example 39 and Example 42, respectively in the patent CN105461702 Å.

Example 1

In 50 mg fruquintinib prepared in Preparation Example 1 added 3.5 ml methanol and 69.8 mg saccharin to form a solution, and the solution was stirred at room temperature for 8 hours and then filtrated under vacuum; the filter cake was vacuum dried at 40° C. for 10 hours to obtain 68.9 mg Compound A of the present invention.

Figure 4:
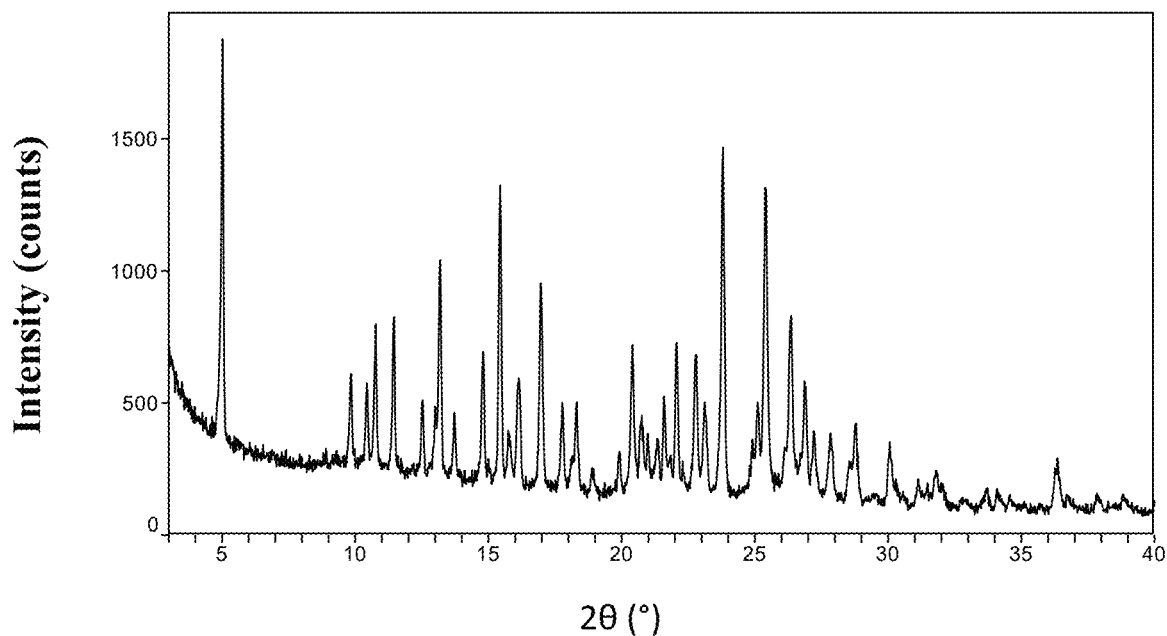
FIG. 4 is the XRPD pattern of the Crystalline Form of Compound A of the present invention.

Its XRPD pattern is shown in FIG. 4, indicating the compound is the crystalline Compound A.

Figure 5:
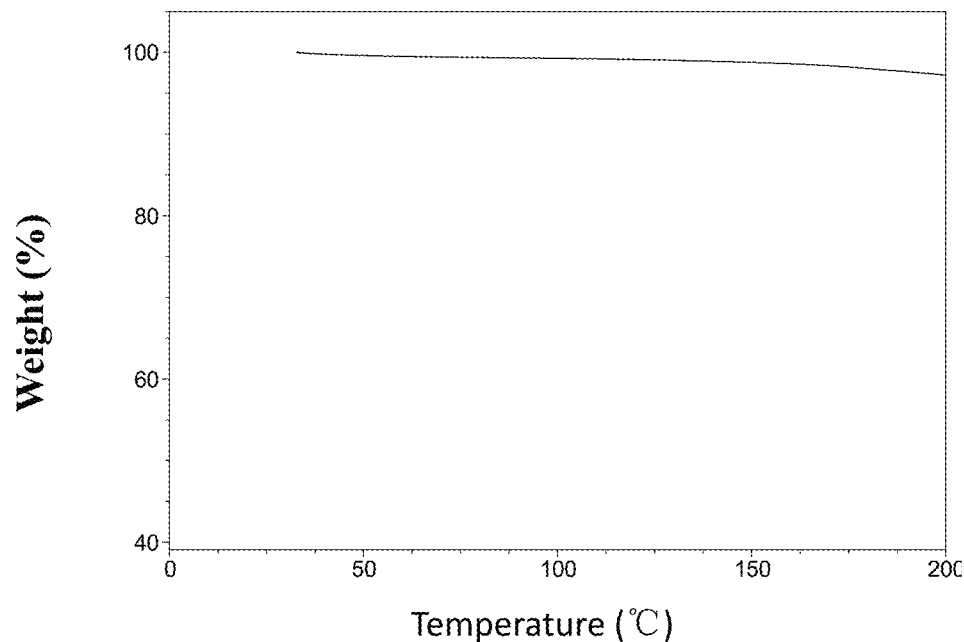
FIG. 5 is the TGA thermogram of the Crystalline Form of Compound A of the present invention.

Its TGA thermogram is shown in FIG. 5.

Figure 6:
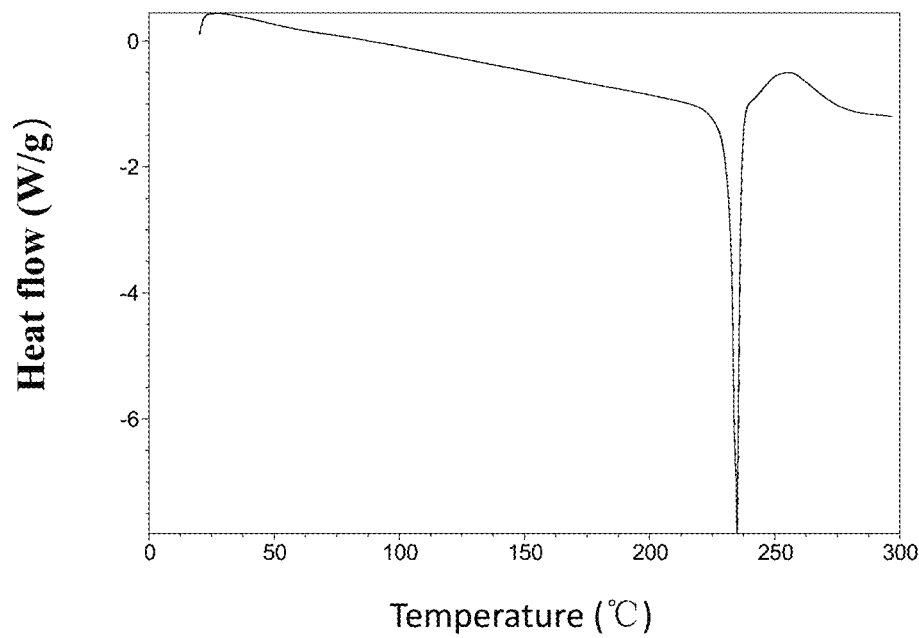
FIG. 6 is the DSC thermogram of the Crystalline Form of Compound A of the present invention.

Its DSC thermogram is shown in FIG. 6.

Figure 7:
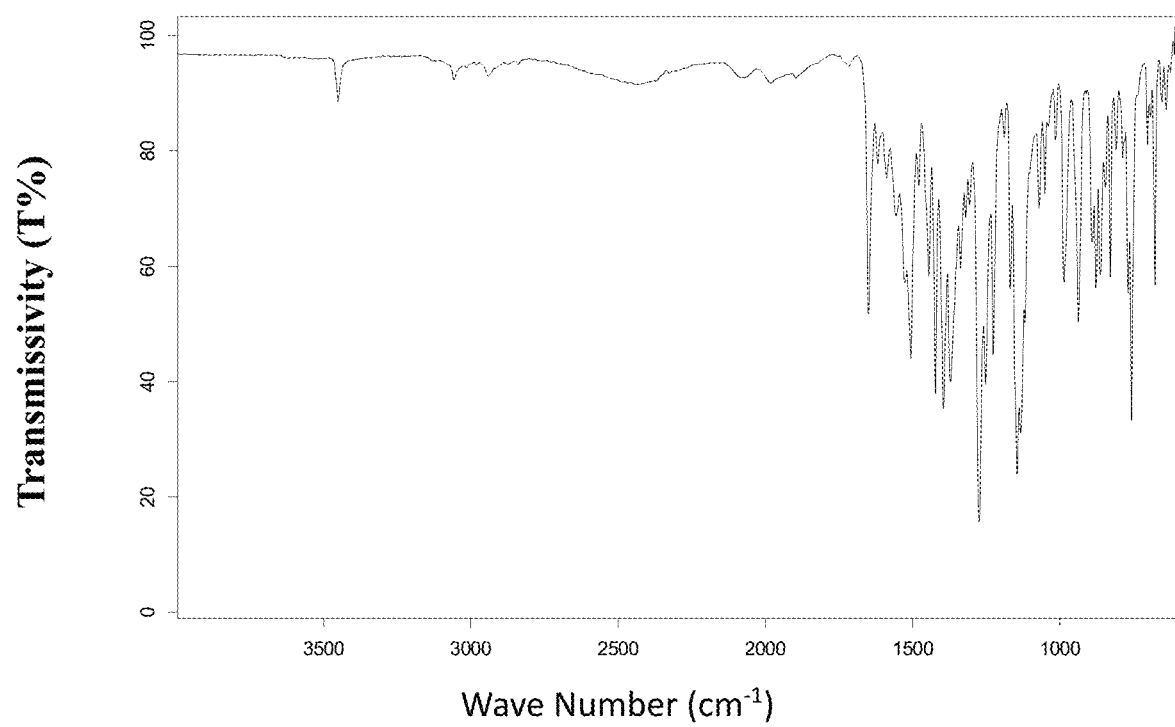
FIG. 7 is the IR spectrum of the Crystalline Form of Compound A of the present invention.

Its IR spectrum is shown in FIG. 7.

Figure 8:
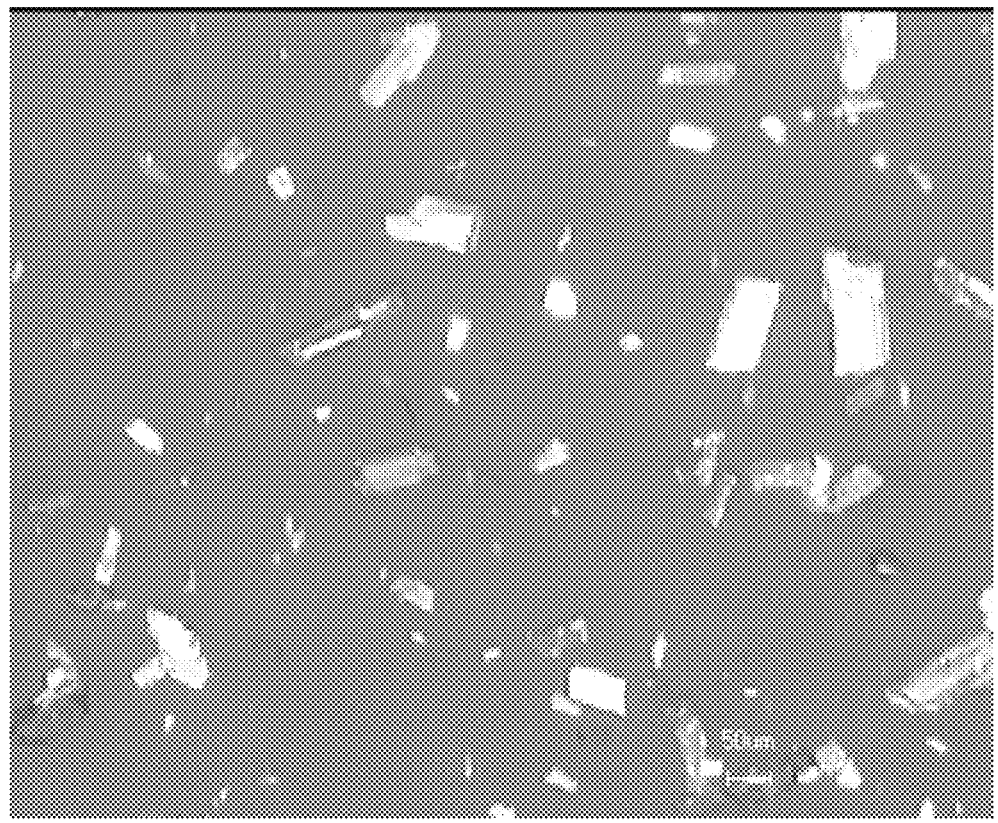
FIG. 8 is the PLM of the Crystalline Form of Compound A of the present invention.

Its PLM is shown in FIG. 8.

Figure 9:
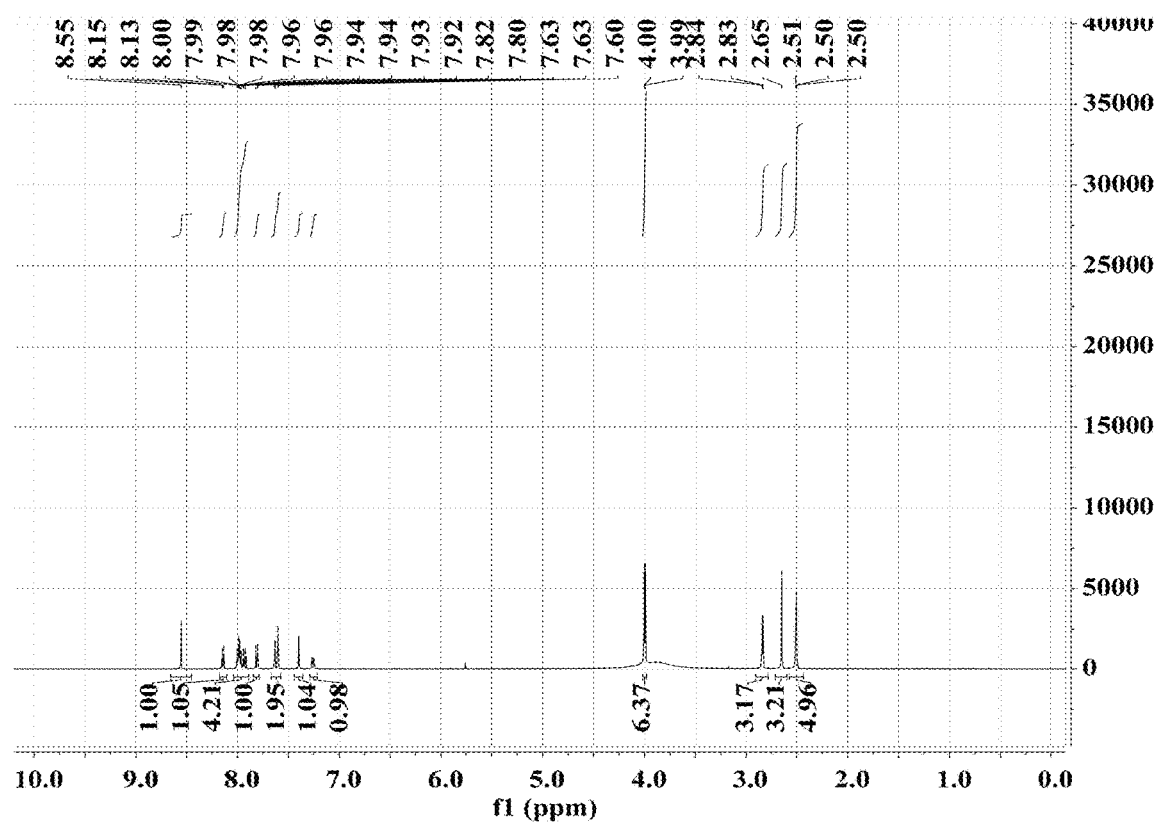
FIG. 9 is the $^1$HNMR spectrum of Compound A of the present invention.

Its $^1$HNMR spectrum is shown in FIG. 9.

Example 2

In 50 mg fruquintinib prepared in Preparation Example 1 added 8.0 ml of methanol and ether mixture (1:1) and 34.9 mg saccharin, stirred at room temperature for 24 hours and then filtrated under vacuum; the filter cake was vacuum dried at 25° C. for 24 hours to obtain 67.3 mg Compound A of the present invention.

Example 3

In 50 mg fruquintinib prepared in Preparation Example 1 added 1.0 ml chloroform and 15.5 mg saccharin, stirred at 40° C. for 24 hours and then filtrated under vacuum; the filter cake was vacuum dried at 30° C. for 20 hours to obtain 42.5 mg Compound A of the present invention.

Example 4

In 50 mg fruquintinib prepared in Preparation Example 1 added 5 ml n-propanol; a saccharin solution (23.3 mg saccharin dissolved in 5.0 ml ethyl acetate) was dripped into the fruquintinib suspension during stirring; stirred at 50° C. for 48 hours and then filtrated under vacuum; the filter cake was vacuum dried at 40° C. for 36 hours to obtain 61.5 mg Compound A of the present invention.

Example 5

Compound A was obtained by replacing the solvent in Example 4 according to the following table.

| No. | Solvent |
| --- | --- |
| Experiment 1 | Mixed solvent of n-butanol and dichloromethane |
| Experiment 2 | Mixed solvent of isopropyl ether and 1,4-dioxane |
| Experiment 3 | Mixed solvent of acetonitrile and butanone |
| Experiment 4 | Mixed solvent of acetone and isopropyl acetate |

Example 6

Added 0.5 ml acetone into 30 mg fruquintinib prepared in Preparation Example 1 and 14.0 mg saccharin to completely wet the mixture at room temperature, ground the mixture until dry to obtain Compound A of the present invention.

Example 7

Completely wetted 30 mg fruquintinib prepared in Preparation Example 1 and 14.0 mg saccharin using 0.2 mL water at room temperature, ground the mixture until dry to obtain Compound A of the present invention.

Example 8

Completely wetted 30 mg fruquintinib prepared in Preparation Example 1 and 14.0 mg saccharin using 2.2 ml tetrahydrofuran at room temperature, ground the mixture until dry to obtain Compound A of the present invention.

Example 9

Compound A was obtained by replacing the solvent in Example 9 according to the following table.

| No. | Solvent |
| --- | --- |
| Experiment 1 | Mixed solventof methanol and isopropyl acetate |
| Experiment 2 | Mixed solvent of n-propanol and chloroform |
| Experiment 3 | Mixed solvent of acetonitrile and ether |
| Experiment 4 | Mixed solvent of ethyl acetate and butanone |
| Experiment 5 | Mixed solvent of isopropyl ether and methanol |
| Experiment 6 | n-heptane |

Example 10

10 mg fruquintinib prepared in Preparation Example 1 was dissolved in 0.5 ml dichloromethane using ultrasonic; a saccharin solution (4.7 mg saccharin dissolved in 0.1 ml methanol) was dripped into the dichloromethane solution of fruquintinib; volatilized at room temperature to obtain Compound A of the present invention.

Example 11

10 mg fruquintinib prepared in Preparation Example 1 and 4.7 mg saccharin were dissolved in 2.2 ml tetrahydrofuran using ultrasonic; volatilized at room temperature to obtain Compound A of the present invention.

Example 12

10 mg fruquintinib prepared in Preparation Example 1 and 4.7 mg saccharin were dissolved in 0.3 ml mixed solvent of trifluoroethanol and methanol (2:1) using ultrasonic, volatilized at 40° C. to obtain Compound A of the present invention.

Example 13

10 mg fruquintinib prepared in Preparation Example 1 and 4.7 mg saccharin were dissolved in 3.0 ml mixed solvent of nitromethane and isopropanol (2:1) using ultrasonic, itvolatilized at 50° C. to obtain Compound A of the present invention.

Example 14

Compound A was obtained by replacing the solvent in Example 13 according to the following table.

| No. | Solvent |
| --- | --- |
| Experiment 1 | Mixed solvent of n-butanol and ether |
| Experiment 2 | Mixed solvent of ethyl acetate and 1,4-dioxane |
| Experiment 3 | Mixed solvent of isopropyl acetate and chloroform |
| Experiment 4 | Mixed solvent of acetone and acetonitrile |
| Experiment 5 | Mixed solvent of butanone and isopropyl ether |

The samples prepared in Examples 2 to 14 had essentially the same or similar XRPD patterns, DSC thermograms, TGA thermograms, IR spectra (not shown) as those of the sample of Example 1, indicating that the samples of Examples 2 to 14 and Example 1 are the same.

Example 15

In 50 mg fruquintinib prepared in Preparation Example 1 added 1.0 ml tetrahydrofuran and 13.2 mg malonic acid, stirred at room temperature for 24 hours and then filtrated under vacuum; the filter cake was vacuum dried at 25° C. for 24 hours to obtain 59.6 mg cocrystal of fruquintinib and malonic acid of the present invention.

Figure 10:
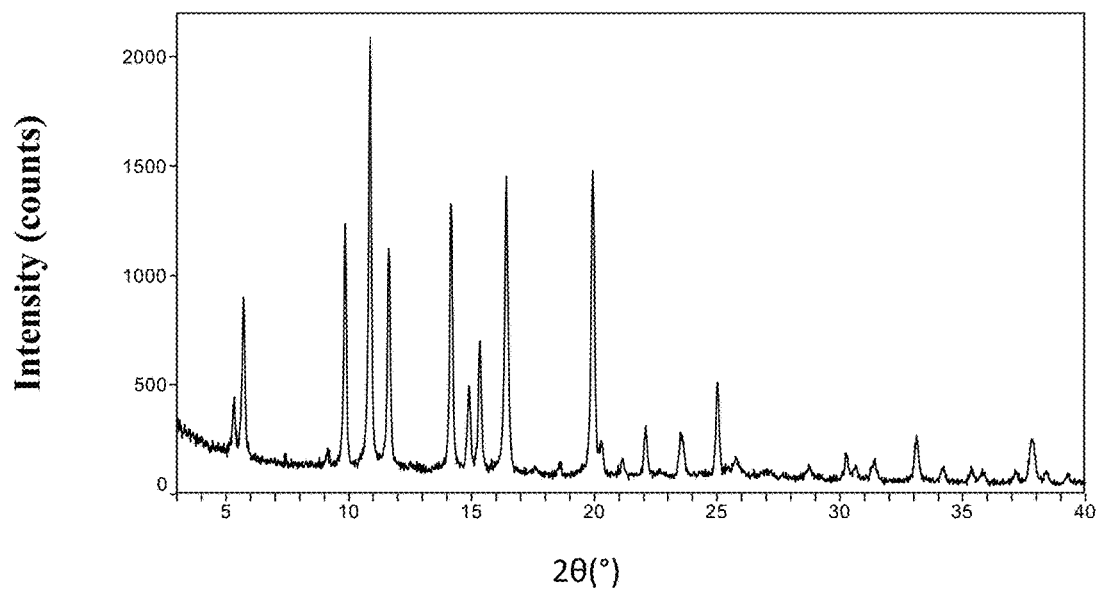
FIG. 10 is the XRPD pattern of the crystalline form of the cocrystal of fruquintinib and malonic acid of the present invention.

The XRPD pattern is shown in FIG. 10, indicating the compound is the crystalline cocrystal of fruquintinib and malonic acid.

Figure 11:
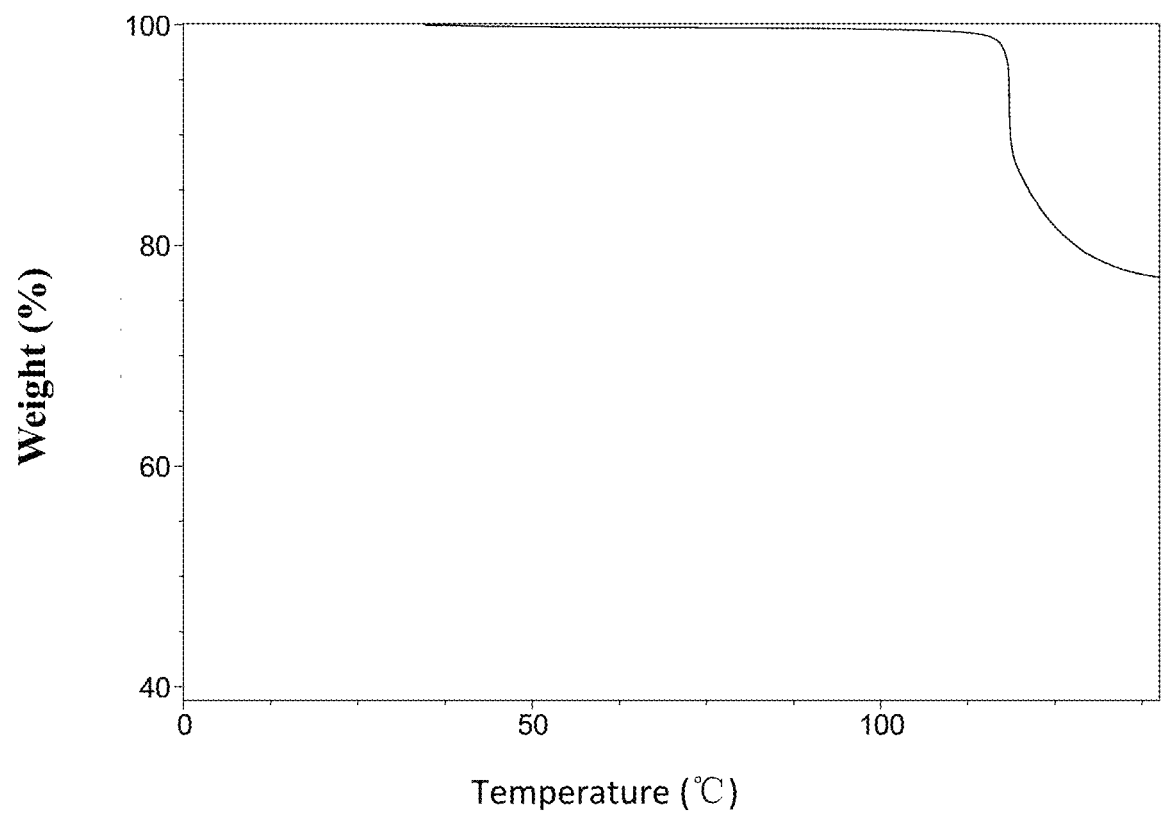
FIG. 11 is the TGA thermogram of the crystalline form of the cocrystal of fruquintinib and malonic acid of the present invention.
Figure 12:
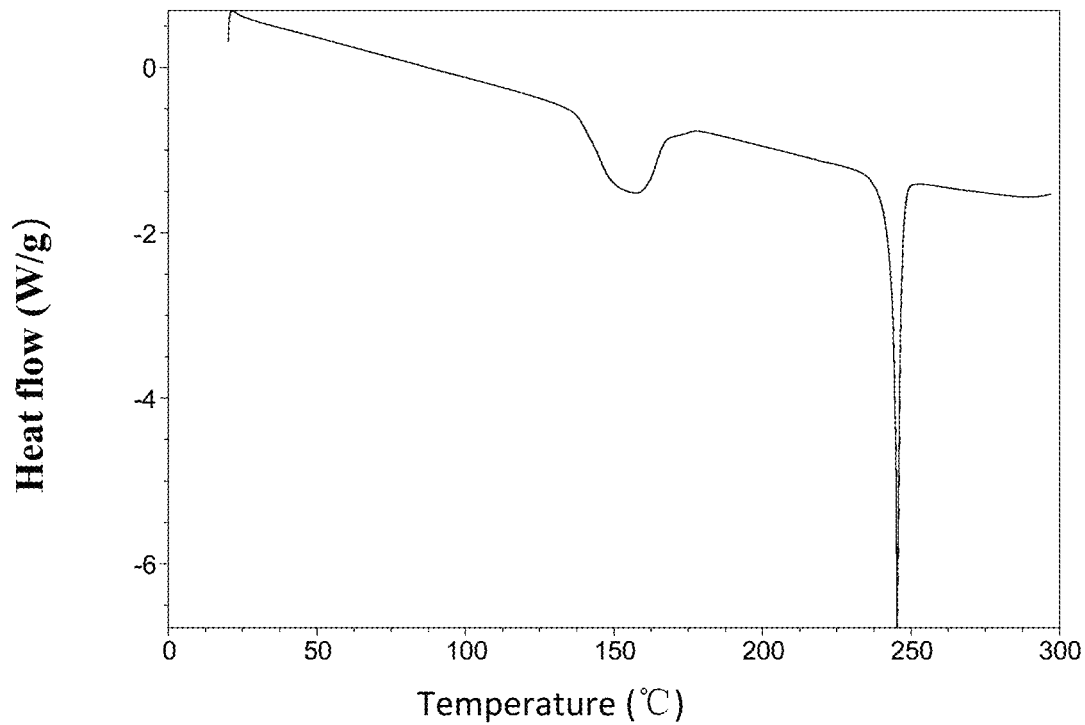
FIG. 12 is the DSC thermogram of the crystalline form of the cocrystal of fruquintinib and malonic acid of the present invention.
Figure 13:
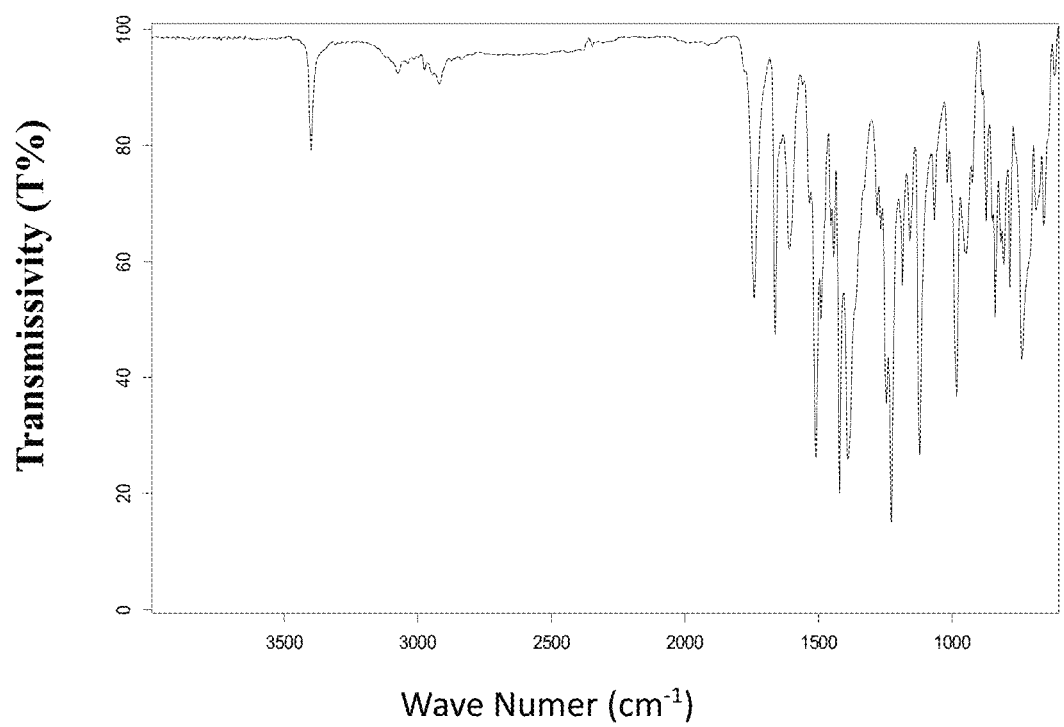
FIG. 13 is the IR spectrum of the crystalline form of the cocrystal of fruquintinib and malonic acid of the present invention.
Figure 14:
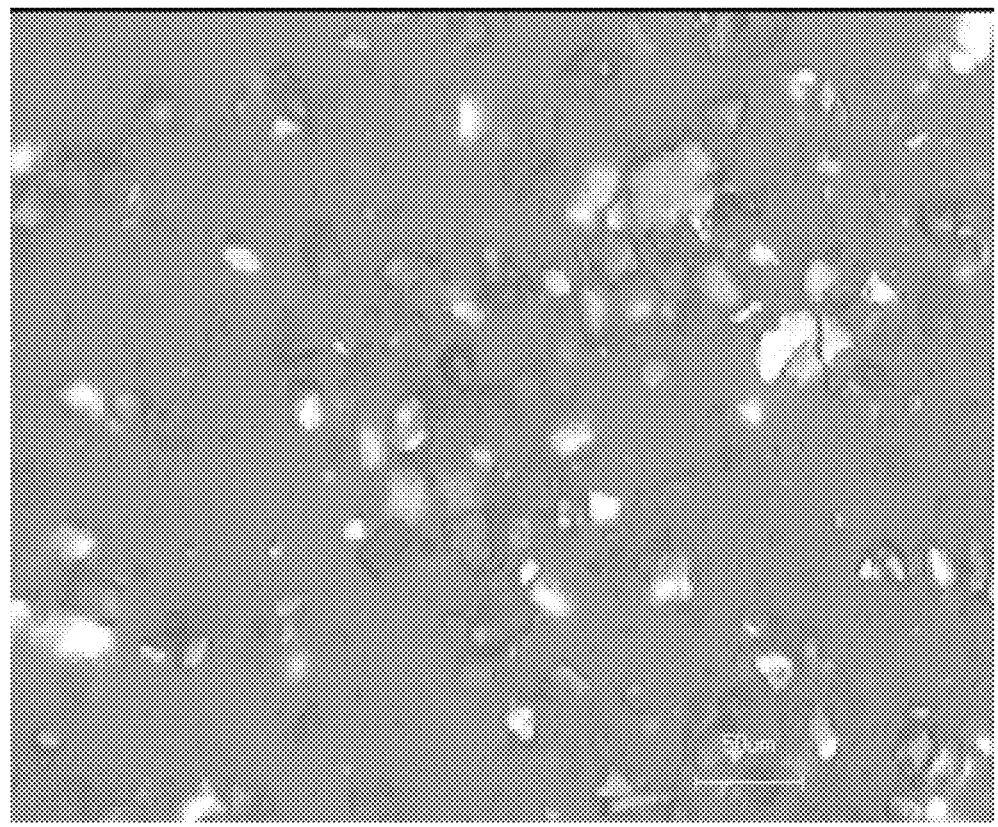
FIG. 14 is the PLM of the crystalline form of the cocrystal of fruquintinib and malonic acid of the present invention.
Figure 15:
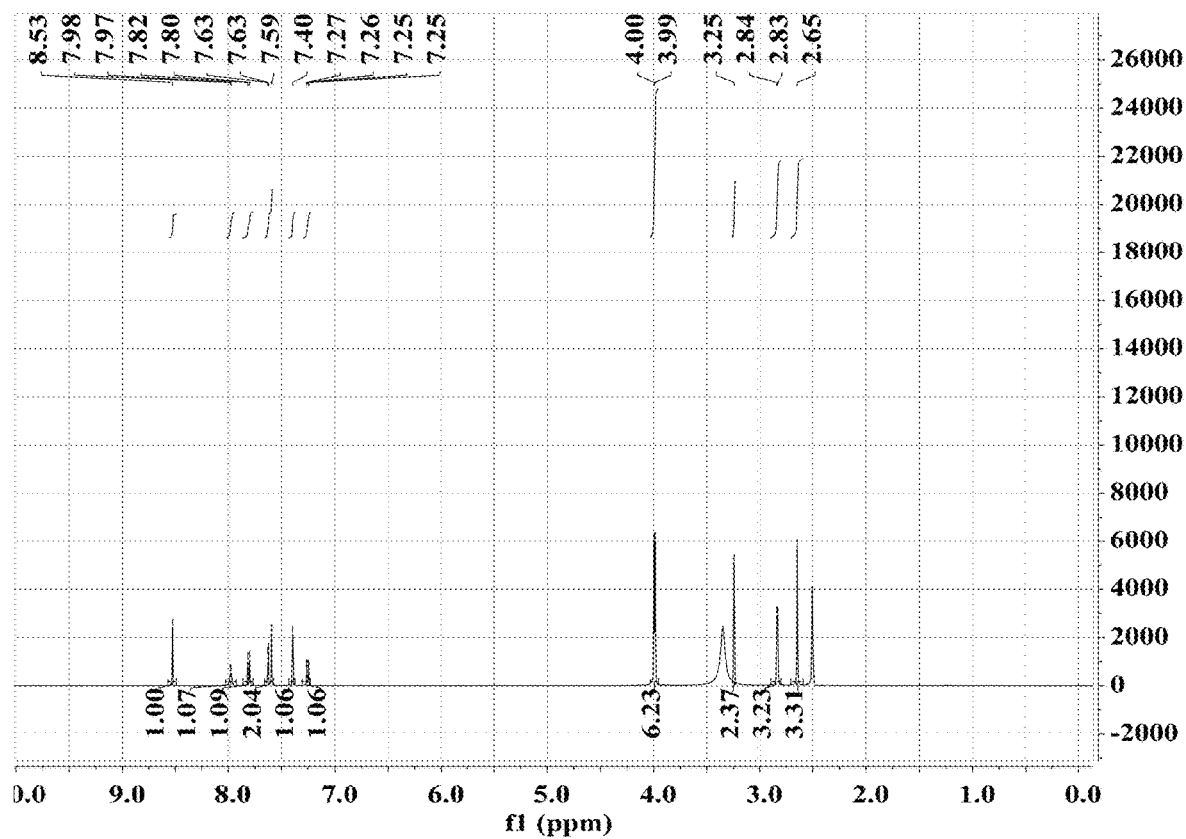
FIG. 15 is the $^1$HNMR spectrum of the crystalline form of the cocrystal of fruquintinib and malonic acid of the present invention.

Its TGA thermogram is shown in FIG. 11.
Its DSC thermogram is shown in FIG. 12.
Its IR spectrum is shown in FIG. 13.
Its PLM is shown in FIG. 14.
Its $^1$HNMR spectrum is shown in FIG. 15.

Example 16

In 50 mg fruquintinib prepared in Preparation Example 1 added 5.3 ml acetone and 26.5 mg malonic acid, then stirred at room temperature for 16 hours and then filtrated under vacuum; the filter cake was vacuum dried at 40° C. for 16 hours to obtain 56.9 mg cocrystal of fruquintinib and malonic acid of the present invention.

Example 17

In 50 mg fruquintinib prepared in Preparation Example 1 added 0.82 ml acetonitrile; a malonic acid solution (33.1 mg malonic acid dissolved in 0.4 ml methanol) was dripped into the fruquintinib suspension during stirring; then stirred at 40° C. for 30 h and then filtrated under vacuum; the filter cake was vacuum dried at 50° C. for 12 hours to obtain 50.8 mg cocrystal of fruquintinib and malonic acid of the present invention.

Example 18

In 50 mg fruquintinib prepared in Preparation Example 1 added 8.2 ml solvent mixture of methyl tert-butyl ether and tetrahydrofuran (1:2); a malonic acid solution (6.6 mg malonic acid dissolved in 1.0 ml solvent mixture of methyl tert-butyl ether and tetrahydrofuran (1:2)) was dripped into the fruquintinib suspension during stirring, then stirred at 50° C. for 42 hours and then filtrated under vacuum; the filter cake was vacuum dried at 45° C. for 20 hours to obtain 33.9 mg cocrystal of fruquintinib and malonic acid of the present invention.

Example 19

The cocrystal of fruquintinib and malonic acid was obtained by replacing the solvent in Example 18 according to the following table.

| No. | Solvent |
| --- | --- |
| Experiment 1 | Mixed solvent of isopropanol and ether |
| Experiment 2 | Mixed solvent of chloroform and butanone |
| Experiment 3 | Mixed solvent of dichloromethane and n-butanol |
| Experiment 4 | Mixed solvent of 1,4-dioxane and ethanol |

Example 20

In 30 mg fruquintinib prepared in Preparation Example 1 and 7.9 mg malonic acid added 1.9 ml acetonitrile to completely wet the mixture at room temperature, then it was ground until dry to obtain the cocrystal of fruquintinib and malonic acid of the present invention.

Example 21

In 30 mg fruquintinib prepared in Preparation Example 1 and 7.9 mg malonic acid added 0.5 ml methanol to completely wet the mixture at room temperature, it was then ground until dry to obtain the cocrystal of fruquintinib and malonic acid of the present invention.

Example 22

In 30 mg fruquintinib prepared in Preparation Example 1 and 7.9 mg malonic acid added 0.15 ml water to completely wet the mixture at 40° C., it was then ground until dry to obtain the cocrystal of fruquintinib and malonic acid of the present invention.

Example 23

The cocrystal of fruquintinib and malonic acid was obtained by replacing the solvent in Example 22 according to the following table.

| No. | Solvent |
| --- | --- |
| Experiment 1 | Mixed solvent of n-propanol and ethyl acetate |
| Experiment 2 | Mixed solvent of isopropyl acetate and methyl cyclohexane |
| Experiment 3 | Mixed solvent of secondary butanol and butanone |
| Experiment 4 | Mixed solvent of acetone and isopropyl ether |
| Experiment 5 | Mixed solvent of chloroform and ether |

Example 24

10 mg fruquintinib prepared in Preparation Example 1 was dissolved in 1.0 ml chloroform using ultrasonic; a malonic acid solution (2.6 mg maleic dissolved in 0.1 ml methanol) was dripped into the dichloromethane solution of fruquintinib; the solution was volatilized at room temperature to obtain the cocrystal of fruquintinib and malonic acid of the present invention.

Example 25

10 mg fruquintinib prepared in Preparation Example 1 and 2.6 mg malonic acid were dissolved in 0.25 ml mixed solvent of acetone and tetrahydrofuran (1:1); after the mixture was dissolved using ultrasonic, it was volatilized at 45° C. to obtain the cocrystal of fruquintinib and malonic acid of the present invention.

Example 26

10 mg fruquintinib prepared in Preparation Example 1 and 2.6 mg malonic acid were dissolved in 12.5 ml mixed solvent of methanol and diethyl ether (15:2); after the mixture was dissolved using ultrasonic, it was volatilized at room temperature to obtain the cocrystal of fruquintinib and malonic acid of the present invention.

Example 27

The cocrystal of fruquintinib and malonic acid was obtained by replacing the solvent in Example 26 according to the following table.

| No. | Solvent |
| --- | --- |
| Experiment 1 | Acetonitrile |
| Experiment 2 | Mixed solvent of dichloromethane and n-butanol |
| Experiment 3 | Mixed solvent of acetone and 1,4-dioxane |
| Experiment 4 | Mixed solvent of tetrahydrofuran and isopropyl ether |
| Experiment 5 | Mixed solvent of butanone and dichloromethane |

The samples prepared in Examples 16 to 27 have essentially the same or similar XRPD patterns, DSC thermograms, TGA thermograms, IR spectra (not shown) as those of the sample of Example 15, indicating that the samples of Examples 16 to 27 and Example 15 are the same.

Example 28

In 50 mg fruquintinib prepared in Preparation Example 1 was added 2.5 ml acetone; a maleic acid solution (14.8 mg maleic acid dissolved in 0.4 ml acetone) was dripped into the acetone solution of fruquintinib; it was then stirred at room temperature for 16 hours and then filtrated under vacuum; the filter cake was vacuum dried at 40° C. for 16 hours to obtain 61.0 mg cocrystal of fruquintinib and maleic acid of the present invention.

Figure 16:
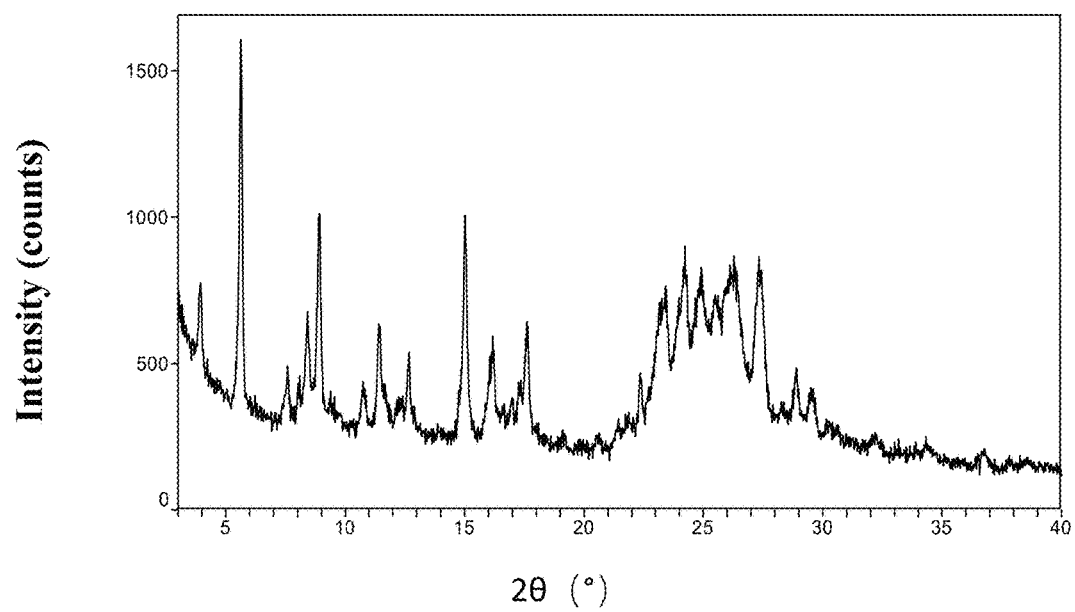
FIG. 16 is the XRPD pattern of the crystalline form of the cocrystal of fruquintinib and maleic acid of the present invention.

The XRPD pattern is shown in FIG. 16, indicating the compound is the crystalline cocrystal of fruquintinib and maleic acid.

Figure 17:
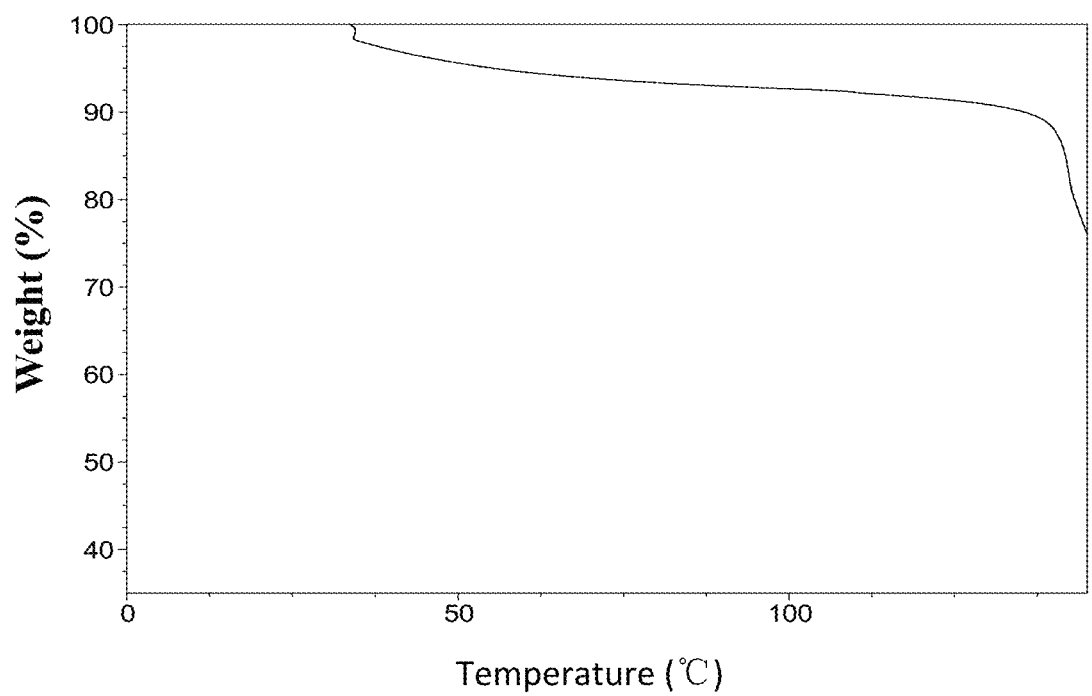
FIG. 17 is the TGA thermogram of the crystalline form of the cocrystal of fruquintinib and maleic acid of the present invention.
Figure 18:
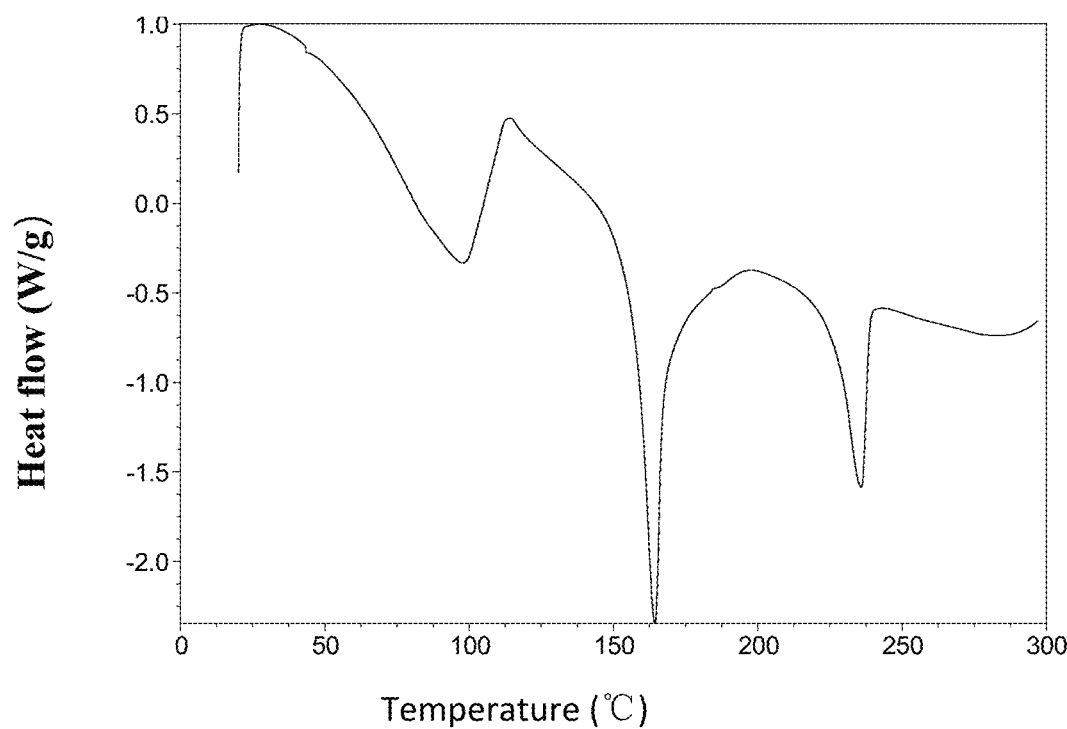
FIG. 18 is the DSC thermogram of the crystalline form of the cocrystal of fruquintinib and maleic acid of the present invention.
Figure 19:
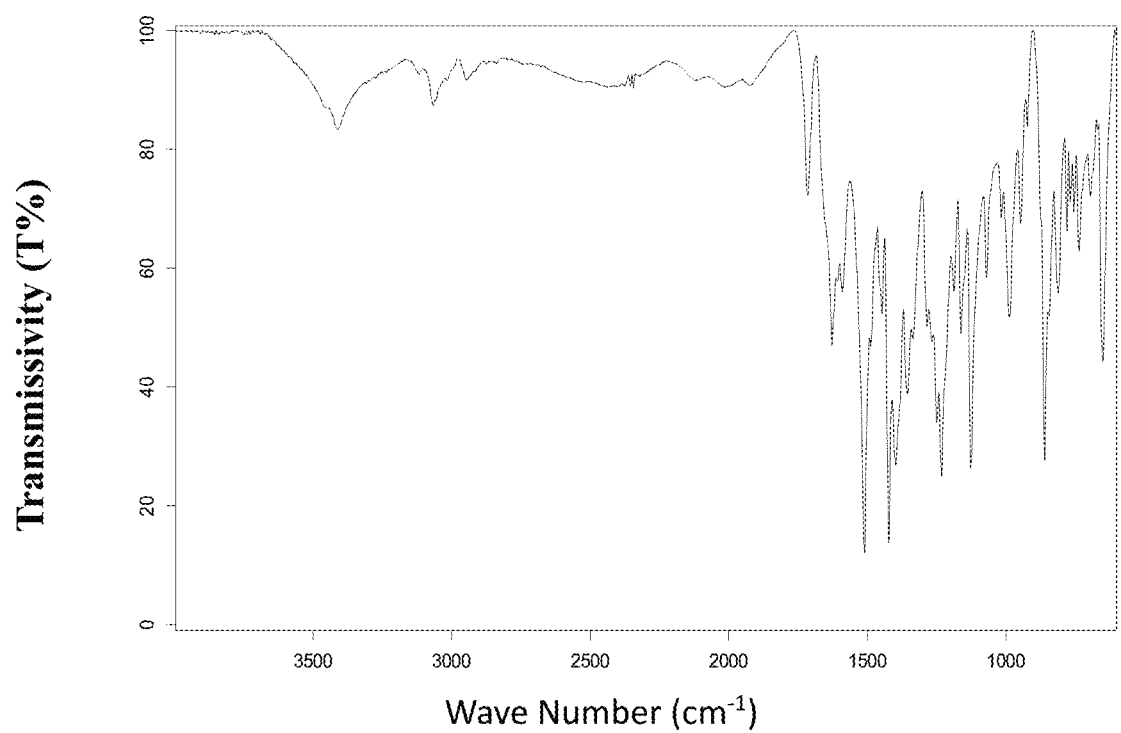
FIG. 19 is the IR spectrum of the crystalline form of the cocrystal of fruquintinib and maleic acid of the present invention.
Figure 20:
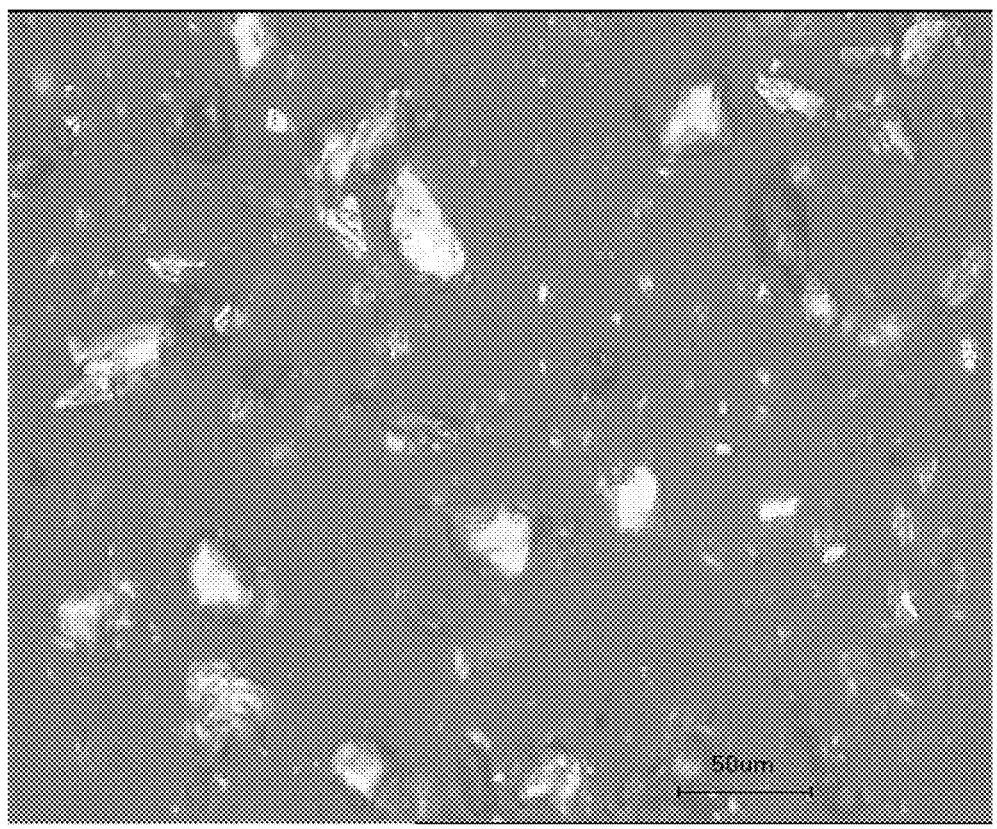
FIG. 20 is the PLM of the crystalline form of the cocrystal of fruquintinib and maleic acid of the present invention.
Figure 21:
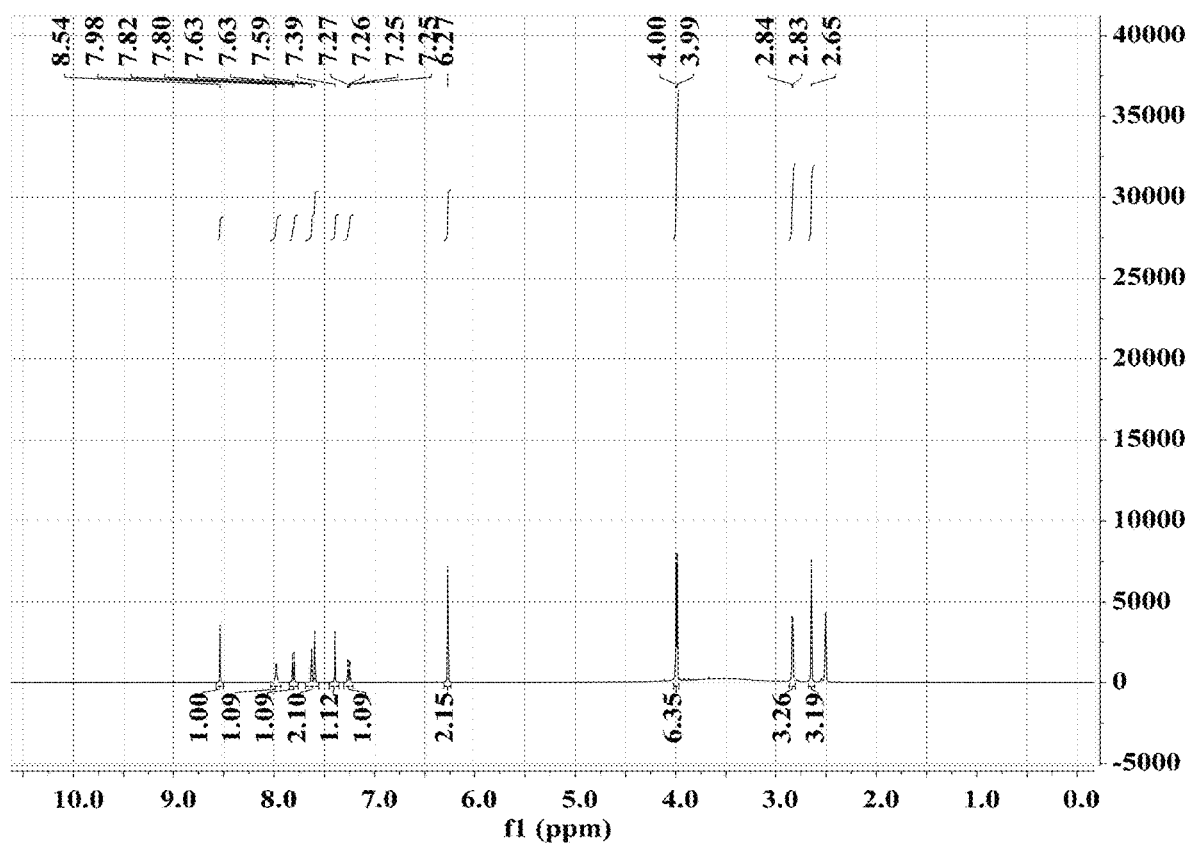
FIG. 21 is the $^1$HNMR spectrum of the crystalline form of the cocrystal of fruquintinib and maleic acid of the present invention.

Its TGA thermogram is shown in FIG. 17.
Its DSC thermogram is shown in FIG. 18.
Its IR spectrum is shown in FIG. 19.
Its PLM is shown in FIG. 20.
Its $^1$HNMR spectrum is shown in FIG. 21.

Example 29

In 50 mg fruquintinib prepared in Preparation Example 1 added 10.0 ml methanol and 29.5 mg maleic acid; it was then stirred at room temperature for 8 hours and then filtrated under vacuum; the filter cake was dried under vacuum at room temperature for 36 hours to obtain 57.6 mg cocrystal of fruquintinib and maleic acid of the present invention.

Example 30

In 50 mg fruquintinib prepared in Preparation Example 1 added 0.8 ml dichloromethane; a maleic acid solution (7.4 mg maleic acid dissolved in 0.2 ml isopropanol) was dripped into the suspension of fruquintinib during stirring; it was then stirred at 45° C. for 30 hours and then filtrated under vacuum; the filter cake was vacuum dried at 60° C. for 12 hours to obtain 47.8 mg cocrystal of fruquintinib and maleic acid of the present invention.

Example 31

In 50 mg fruquintinib prepared in Preparation Example 1 added 1.4 ml solvent mixture of acetonitrile:and methanol (1:1); a maleic acid solution (44.3 mg maleic acid dissolved in 0.8 ml acetonitrile and methanol (1:1)) was dripped into the suspension of fruquintinib during stirring; it was then stirred at 50° C. for 48 hours and then filtrated under vacuum; the filter cake was vacuum dried at 45° C. for 30 hours to obtain 52.4 mg cocrystal of fruquintinib and maleic acid of the present invention.

Example 32

The cocrystal of fruquintinib and maleic acid was obtained by replacing the solvent in Example 31 according to the following table.

| No. | Solvent |
| --- | --- |
| Experiment 1 | Acetonitrile |
| Experiment 2 | Mixed solvent of secondary butanol and acetone |
| Experiment 3 | Mixed solvents of chloroform and butanone |
| Experiment 4 | Mixed solvents of dichloromethane and n-butanol |

Example 33

In 30 mg fruquintinib prepared in Preparation Example 1 and 8.9 mg maleic acid added 1.0 ml isopropanol to completely wet the mixture at room temperature, it was then ground until dry to obtain the cocrystal of fruquintinib and maleic acid of the present invention.

Example 34

In 30 mg fruquintinib prepared in Preparation Example 1 and 8.9 mg maleic acid added 1.9 ml acetone to completely wet the mixture at room temperature, it was then ground until dry to obtain the cocrystal of fruquintinib and maleic acid of the present invention.

Example 35

In 30 mg fruquintinib prepared in Preparation Example 1 and 8.9 mg maleic acid added 0.19 ml methanol to completely wet the mixture at 40° C., it was then ground until dry to obtain the cocrystal of fruquintinib and maleic acid of the present invention.

Example 36

The cocrystal of fruquintinib and maleic acid was obtained by replacing the solvent in Example 35 according to the following table.

| No. | Solvent |
| --- | --- |
| Experiment 1 | Water |
| Experiment 2 | N-heptane |
| Experiment 3 | Mixed solvent of isopropanol and methyl cyclohexane |
| Experiment 4 | Mixed solvents of methanol and tetrahydrofuran |
| Experiment 5 | Mixed solvent of n-butanol and ethyl acetate |
| Experiment 6 | Mixed solvent of isopropyl acetate and ether |
| Experiment 7 | Mixed solvent of isopropyl ether and acetone |
| Experiment 8 | Mixed solvent of butanone and acetonitrile |

Example 37

10 mg fruquintinib prepared in Preparation Example 1 was dissolved in 0.8 ml dichloromethane using ultrasound;

a maleic acid solution (3.0 mg maleic acid dissolved in 0.2 ml methanol) was dripped into the dichloromethane solution of fruquintinib; it was then volatilized at room temperature to obtain the cocrystal of fruquintinib and maleic acid of the present invention.

Example 38

In 10 mg fruquintinib prepared in Preparation Example 1 and 3.0 mg maleic acid added 13.0 ml mixed solvent of isopropanol and chloroform (1:4); after the mixture was dissolved using ultrasonic, it was volatilized at room temperature to obtain the cocrystal of fruquintinib and maleic acid of the present invention.

Example 39

In 10 mg fruquintinib prepared in Preparation Example 1 and 3.0 mg maleic acid added 0.26 ml mixed solvent of chloroform and tetrahydrofuran (1:1); after the mixture was dissolved using ultrasonic, it was volatilized at 50° C. to obtain the cocrystal of fruquintinib and maleic acid of the present invention.

Example 40

The cocrystal of fruquintinib and maleic acid was obtained by replacing the solvent in Example 39 according to the following table.

| No. | Solvent |
| --- | --- |
| Experiment 1 | Isopropyl alcohol |
| Experiment 2 | Acetone |
| Experiment 3 | Mixed solvent of butanone and tetrahydrofuran |
| Experiment 4 | Mixed solvent of 1,4-dioxane and chloroform |
| Experiment 5 | Mixed solvent of n-butanol and acetonitrile |

The samples prepared in Examples 29 to 40 have essentially the same or similar XRPD patterns, DSC thermograms, TGA thermograms, IR spectra (not shown) as those of the sample of Example 28, indicating that the samples of Examples 29 to 40 and Example 28 are the same.

Example 41

Hard-shell capsule: A large number of capsules was prepared by filling traditional two-piece hard-shell capsules. The dosage unit contains 5 mg active pharmaceutical ingredient (7.3 mg Compound A of the present invention), 150 mg lactose, 50 mg cellulose and 3 mg magnesium stearate.

Example 42

Hard-shell capsule: The amount of the active pharmaceutical ingredient in Example 41 was changed to 4 mg (5.9 mg Compound A of the present invention), and the other operations were the same as those of Example 41.

Example 43

Hard-shell capsule: The amount of the active pharmaceutical ingredient in Example 41 was changed to 1 mg (1.5 mg Compound A of the present invention), and the other operations were the same as those of Example 41.

Examples 44-49

Hard-shell capsule: Compound A in Examples 41 to 43 was respectively replaced by the cocrystal of fruquintinib and malonic acid of the present invention or the cocrystal of fruquintinib and maleic acid of the present invention. The free bases in the formulation of the cocrystal of fruquintinib and malonic acid of the present invention or the cocrystal of fruquintinib and maleic acid of the present invention and in the formulation of Compound A have the same molar amount, and the total amount of the co-crystal and the fillers in these formulations is the same as the total amount in formulation of Compound A, and other preparation steps are the same as those in the Examples 41 to 43.

Exchange 50

Soft gelatin capsule: A mixture of active ingredients was prepared in digestible oil such as soybean oil, cottonseed oil or olive oil and molten gelatin was pumped by active displacement pump to form a soft gelatin capsules containing 5 mg active pharmaceutical ingredient (7.3 mg Compound A of the present invention). The capsule was washed and dried. The active pharmaceutical ingredient can be dissolved in a mixture of polyethylene glycol, glycerin and sorbitol to prepare a pharmaceutical mixture able to be mixed with water.

Example 51

Soft gelatin capsule: The amount of the active pharmaceutical ingredient in Example 50 was changed to 4 mg (5.9 mg Compound A of the present invention), and the other operations were the same as those of Example 50.

Example 52

Soft gelatin capsule: The amount of the active pharmaceutical ingredient in Example 50 was changed to 1 mg (1.5 mg Compound A of the present invention), and the other operations were the same as those of Example 50.

Examples 53-58

Hard-shell capsule: Compound A in Examples 50 to 52 was respectively replaced by the cocrystal of fruquintinib and malonic acid of the present invention or the cocrystal of fruquintinib and maleic acid of the present invention. The free bases in the formulation of the cocrystal of fruquintinib and malonic acid of the present invention or the cocrystal of fruquintinib and maleic acid of the present invention and in the formulation of Compound A have the same molar amount, and the total amount of the co-crystal and the fillers in these formulations is the same as the total amount in formulation of Compound A, and other preparation steps are the same as those in the Examples 50 to 52.

Example 59

Tablet: A large number of tablets were prepared by conventional processes such that the dosage unit was 5 mg active pharmaceutical ingredient (7.3 mg Compound A of the present invention), 1 mg colloidal silica, 2 mg magnesium stearate, 100 mg microcrystalline cellulose, 10 mg starch and 50 mg lactose. Appropriate aqueous or non-aqueous coating could be used to improve palatability, improve appearance and stability or delay absorption.

Example 60

Tablet: The amount of the active pharmaceutical ingredient in Example 59 was changed to 4 mg (5.9 mg Compound A of the present invention), and the other operations were the same as those of Example 59.

Example 61

Tablet: The amount of the active pharmaceutical ingredient in Example 59 was changed to 1 mg (1.5 mg Compound A of the present invention), and the other operations were the same as those of Example 59.

Examples 62-67

Tablet: Hard-shell capsule: Compound A in Examples 59 to 61 was respectively replaced by the cocrystal of fruquintinib and malonic acid of the present invention or the cocrystal of fruquintinib and maleic acid of the present invention. The free bases in the formulation of the cocrystal of fruquintinib and malonic acid of the present invention or the cocrystal of fruquintinib and maleic acid of the present invention and in the formulation of Compound A have the same molar amount, and the total amount of the co-crystal and the fillers in these formulations is the same as the total amount in formulation of Compound A, and other preparation steps are the same as those in the Examples 59 to 61.

Example 68

Immediate Release Tablet/Capsule:

This solid oral dosage form was prepared by conventional and new processes. These dosage units are taken orally and rapidly break down. The active pharmaceutical ingredient was mixed with liquids containing such as sugar, gelatin, pectin and sweetener. These liquids were solidified into solid tablets or caplets by freeze-drying and solid extraction techniques. The pharmaceutical compounds can be compressed with viscoelastic and thermoelastic sugars and polymers or effervescent ingredients to produce a porous matrix for rapid release that does not require water. Active pharmaceutical ingredients included the Compounds A, cocrystal of fruquintinib and malonic acid and cocrystal of fruquintinib and maleic acid of the present invention.

Example 69

Sustained Release Tablet/Capsule:

This kind of solid oral dosage form was prepared by conventional and new processes.

These dosage units are taken orally to release slowly and deliver the drug. The active pharmaceutical ingredient was mixed with one or more solids such as starch, sugar or other hygroscopic agent, prepared into solid dispersion by aqueous hypromellose solution or by ethylcellulose ethanol solution, then prepared into solid tablets or caplets by wet granulation. Active pharmaceutical ingredients included the Compounds A, cocrystal of fruquintinib and malonic acid and cocrystal of fruquintinib and maleic acid of the present invention.

Example 70

Sterile IV Solution:

Compound A in the present invention was formulated into a 2.5 mg/ml solution with sterile water for injection, meanwhile 2 wt % of solubilizer Pluronic F-68 was added and the pH value was adjusted as needed. For administration, the above solution was diluted with 5% sterile dextrose to 0.5 to 2.5 mg/ml and administered as an intravenous infusion over 10 to 30 minutes.

Examples 71-72

Sterile IV solution: Compound A in Example 70 was respectively replaced by the cocrystal of fruquintinib and malonic acid of the present invention or the cocrystal of fruquintinib and maleic acid of the present invention. The free bases in the formulation of the cocrystal of fruquintinib and malonic acid of the present invention or the cocrystal of fruquintinib and maleic acid of the present invention and in the formulation of Compound A have the same molar amount, and the total amount of the co-crystal and the fillers in these formulations is the same as the total amount in formulation of Compound A, and other preparation steps are the same as those in Example 70.

Example 73

Lyophilized powder for intravenous administration: (i) 135-1350 mg Compound A of the present invention in the form of lyophilized powder, (ii) 32-327 mg/ml sodium citrate, and (iii) 300-3000 mg dextran 40 could be used to make a sterile preparation. Compound A of the present invention was added with sterile injection water or 5% dextrose to a concentration of 6 to 13 mg/ml, further diluted with saline or 5% dextran to a concentration of 0.1 to 0.6 mg/ml, and was administered by intravenous bolus or intravenous infusion for 10 to 30 minutes.

Examples 74-75

Lyophilized powder for intravenous administration: Compound A in Example 73 was respectively replaced by the cocrystal of fruquintinib and malonic acid of the present invention or the cocrystal of fruquintinib and maleic acid of the present invention. The free bases in the formulation of the cocrystal of fruquintinib and malonic acid of the present invention or the cocrystal of fruquintinib and maleic acid of the present invention and in the formulation of Compound A have the same molar amount, and the total amount of the co-crystal and the fillers in these formulations is the same as the total amount in formulation of Compound A, and other preparation steps are the same as those in Example 73.

Example 76

Intramuscular suspension: For intramuscular injection, the following solutions or suspensions could be prepared:
1 mg/ml such as Compound A of the present invention (insoluble in water)
0.5 mg/ml sodium carboxymethylcellulose
0.1 mg/ml Tween80
9 mg/ml sodium chloride
9 mg/ml benzyl alcohol

Examples 77-78

Intramuscular suspension: Compound A in Example 76 was respectively replaced by the cocrystal of fruquintinib and malonic acid of the present invention or the cocrystal of fruquintinib and maleic acid of the present invention. The free bases in the formulation of the cocrystal of fruquintinib and malonic acid of the present invention or the cocrystal of fruquintinib and maleic acid of the present invention and in the formulation of Compound A have the same molar amount, and the total amount of the co-crystal and the fillers in these formulations is the same as the total amount in formulation of Compound A, and other preparation steps are the same as those in Example 76.

Example 79

A proper amount of Compound A of the present invention was dissolved in a mixed solution of tetrahydrofuran and chloroform to form a solution; and the solution was volatized at 40° C. through a small hole to obtain the single crystal of Compound A.

The single crystal parameters are shown in Table 1 and the atomic coordinates are shown in Table 2.

TABLE 1

Single Crystal Parameters of Compound A
Crystal Parameters

| | |
|---|---|
| Molecular component | $C_{21}H_{19}O_5N_3 \cdot C_7H_5O_3NS$ |
| Molecular weight (g/mol) | 576.58 |
| Crystal system | Triclinic |
| Space group | P1 |
| Temperature/K | 106.3 |
| a/Å | 8.6146(10) |
| b/Å | 8.9574(11) |
| c/Å | 17.310(2) |
| α/° | 84.030(10) |
| β/° | 77.369(10) |
| γ/° | 77.771(10) |
| Z | 2 |
| V/Å$^3$ | 1271.5(3) |
| $D_{calc}$/g cm$^{-3}$ | 1.519 |

In Table 2, a, b and c are for e axis length, α, β and γ are dihedral angle, Z for the number of molecules in unit of $C_{21}H_{19}O_5N_3 \cdot C_7H_5O_3NS$ in each unit cell, V for cell volume and $D_{calc}$ for unit cell density.

Single crystal analytical parameters: residual factor R1=0.0702, weighted R value wR$^2$=0.1282, goodness of fit GooF(S)=1.037, S value close to 1, indicating that single crystal data are reasonable.

TABLE 2

Atomic Coordinates of Compound A

| Atom | X | Y | Z |
|---|---|---|---|
| S1 | 6100.9(8) | 419.7(7) | 2756.2(4) |
| O2 | 9429(2) | 3065(2) | 6171.2(11) |
| O6 | 6049(2) | −2480(2) | 4413.6(11) |
| O3 | 9537(2) | −2321(2) | 7420.0(11) |
| O1 | 8070(2) | 3208(2) | 4983.8(11) |
| O4 | 7059(2) | −5470(2) | 9582.4(12) |
| N2 | 8512(3) | −3534(2) | 6587.1(13) |
| O7 | 4897(2) | 1813(2) | 2760.3(12) |
| O8 | 7683(2) | 510(2) | 2275.2(11) |
| N1 | 7591(3) | −2099(2) | 5500.2(12) |
| O5 | 12063(3) | −8357(3) | 9779.7(14) |
| N3 | 10143(3) | −8958(3) | 10805.5(13) |
| C5 | 7746(3) | 570(3) | 5194.7(14) |
| C3 | 8703(3) | −862(3) | 6337.2(15) |
| N4 | 6269(3) | −248(3) | 3653.4(13) |
| C12 | 8130(3) | −3847(3) | 8451.1(16) |
| C1 | 7877(3) | −3388(3) | 5941.8(15) |
| C25 | 4948(3) | −1377(3) | 1802.5(17) |
| C4 | 8003(3) | −795(3) | 5671.4(15) |
| C6 | 8235(3) | 1827(3) | 5387.4(15) |
| C8 | 9198(3) | 429(3) | 6527.6(15) |
| C7 | 8983(3) | 1756(3) | 6062.6(15) |
| C23 | 5332(3) | −2188(3) | 3140.5(15) |
| C22 | 5908(3) | −1646(3) | 3795.1(15) |
| C11 | 9571(3) | −3603(3) | 7969.7(15) |
| C2 | 8884(3) | −2285(3) | 6779.5(14) |
| C14 | 9789(3) | −5924(3) | 9138.3(15) |
| C10 | 10097(3) | 3049(3) | 6863.5(16) |
| C16 | 11079(3) | −4444(3) | 8050.6(16) |
| C21 | 11280(4) | −10098(3) | 11164.3(16) |
| C28 | 4819(3) | −3542(3) | 3114.9(17) |
| C27 | 4359(3) | −3812(3) | 2427.7(18) |
| C13 | 8307(3) | −5027(3) | 9030.2(16) |
| C15 | 11205(3) | −5626(3) | 8636.2(16) |
| C9 | 7228(3) | 3394(3) | 4334.0(16) |
| C19 | 10631(3) | −8145(3) | 10138.9(16) |
| C17 | 9394(3) | −6970(3) | 9820.5(16) |
| C24 | 5383(3) | −1131(3) | 2493.8(16) |
| C26 | 4432(4) | −2749(4) | 1782.2(18) |
| C18 | 7767(4) | −6659(4) | 10055.7(18) |
| C20 | 6565(4) | −7323(5) | 10676(2) |
| O9 | 5056(11) | 675(10) | 156(5) |
| H1 | 7130 | −2082 | 5092 |
| H3 | 9108 | −8797 | 11032 |
| H5 | 7247 | 623 | 4752 |
| H12 | 7104 | −3257 | 8390 |
| H1A | 7610 | −4273 | 5786 |
| H25 | 4997 | −649 | 1362 |
| H8 | 9678 | 380 | 6977 |
| H10A | 9236 | 3042 | 7339 |
| H10B | 10567 | 3962 | 6838 |
| H10C | 10942 | 2131 | 6886 |
| H16 | 12029 | −4213 | 7705 |
| H21A | 12120 | −10619 | 10747 |
| H21B | 10704 | −10848 | 11494 |
| H21C | 11785 | −9600 | 11495 |
| H28 | 4782 | −4270 | 3556 |
| H27 | 3992 | −4729 | 2400 |
| H15 | 12234 | −6216 | 8692 |
| H9A | 6132 | 3190 | 4530 |
| H9B | 7821 | 2675 | 3931 |
| H9C | 7160 | 4444 | 4100 |
| H26 | 4125 | −2960 | 1316 |
| H20A | 6477 | −6889 | 11184 |
| H20B | 6921 | −8436 | 10728 |
| H20C | 5505 | −7081 | 10523 |

Comparation Example 1

The fruquintinib Crystalline Form I, Crystalline Form III and Crystalline Form VII prepared in Preparation Example 2, as well as the Crystalline Form of Compound A of the present invention, the crystalline form of the cocrystal of fruquintinib and malonic acid of the present invention and the crystalline form of the cocrystal of fruquintinib and maleic acid were respectively dissolved in water for solubility experiment. The specific operation steps: respectively took 10 mg of each of the above samples and put them into a 20 ml glass bottle respectively, added 10 ml deionized water, placed the solution at 25° C. ultrasound for 1 min, then took the samples for filtration and analyzed their concentrations using HPLC; calculated their solubility in water respectively.

TABLE 3

Solubility in Water

| Sample name | Solubility (ug/mL) |
| --- | --- |
| Known fruquintinib Crystalline Form I | 2.2 |
| Known fruquintinib Crystalline Form III | 2.1 |
| Known fruquintinib Crystalline Form VII | 2.6 |
| Crystalline Form of Compound A of the present invention | 9.9 |
| Crystalline form of the cocrystal of fruquintinib and malonic acid of the present invention | 12.0 |
| Crystalline form of the cocrystal of fruquintinib and maleic acid of the present invention | 9.4 |

According to Table 3, compared with the known fruquintinib Crystalline Form I, Form III and Form VII, Compound A, the cocrystal of fruquintinib and malonic acid and the cocrystal of fruquintinib and maleic acid of the present invention have about 4 to 6 times higher in solubility, indicating that they have better water solubility and thus better bioavailability.

Comparation Example 2

The fruquintinib mono acetic acid solvate (Crystalline Form IV) prepared in Preparation Example 2, as well as the Crystalline Form of Compound A of the present invention, the crystalline form of the cocrystal of fruquintinib and malonic acid of the present invention and the crystalline form of the cocrystal of fruquintinib and maleic acid were respectively stirred in water for crystal slurry experiment. The specific operation steps: respectively took 10 mg of each of the above samples and put them into a 5 ml glass bottle respectively, added 2 ml deionized water, stirred the solution at room temperature for 24 hours, then took the samples for filtration; and analyzed their crystalline forms with XRD.

TABLE 4

Crystalline Form Stability

| Sample name | XRD test result |
| --- | --- |
| Known fruquintinib monoacetate (Crystalline Form IV) | Known fruquintinib Crystalline Form I |
| Compound A's CrystallineForm of the present invention | Crystalline Form of Compound A of the present invention |
| Ccrystalline form of the cocrystal of fruquintinib and malonic acid of the present invention | Crystalline form of the cocrystal of fruquintinib and malonic acid of the present invention |
| Ccrystalline form of the cocrystal of fruquintinib and maleic acid of the present invention | Crystalline form of the cocrystal of fruquintinib and maleic acid of the present invention |

According to Table 4, compared with the Known fruquintinib mono acetic acid solvate (Crystalline Form IV), the Crystalline Form of Compound A, the crystalline form of the cocrystal of fruquintinib and malonic acid and the crystalline form of the cocrystal of fruquintinib and maleic acid of the present invention have better crystalline form stability and thus may have better process operability.

All the patents, patent application disclosures, patent applications and non-patented publications cited in this document are incorporated into this document by citation in full.

The above mentioned are only the embodiments of the present invention, which do not cover the entire protection scope of the present invention. Within the technical scope revealed in the present invention, modifications or replacements made by those skilled in the art without creative labor should all be within the protection scope of the present invention. Therefore, these shall be made within the scope of the present invention defined by the claims.

The invention claimed is:

1. Compound A formed by fruquintinib and saccharin having the structure shown below:

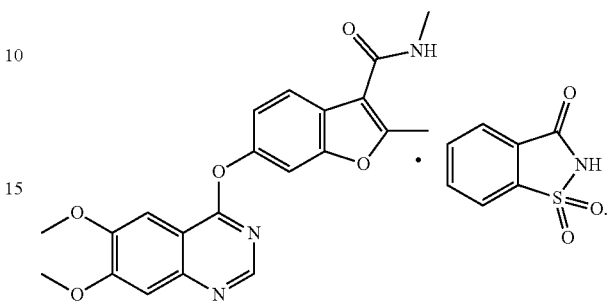

2. Compound A according to claim 1, wherein compound A is a cocrystal or salt.

3. Compound A according to claim 1, wherein the X-ray powder diffraction pattern of the crystalline form of compound A, expressed as 2θ angles, has the following characteristic peaks: 5.0±0.2°, 13.2±0.2°, 15.4±0.2° and 17.0±0.2°.

4. Compound A according to claim 3, wherein the X-ray powder diffraction pattern of the crystalline form of compound A, expressed as 2θ angles, further comprises the following characteristic peaks: 10.8±0.2°, 11.5±0.2, 14.8±0.2°, 23.8±0.2° and 25.4±0.2°.

5. Compound A according to claim 4, wherein the X-ray powder diffraction pattern of the crystalline form of compound A, expressed as 2θ angles, has the following characteristic peaks and relative intensities:

| 2θ | Relative intensity % |
| --- | --- |
| 5.0 ± 0.2° | 100.0 |
| 9.8 ± 0.2° | 22.4 |
| 10.4 ± 0.2° | 20.1 |
| 10.8 ± 0.2° | 35.3 |
| 11.5 ± 0.2° | 37.9 |
| 12.5 ± 0.2° | 18.3 |
| 13.2 ± 0.2° | 54.3 |
| 13.7 ± 0.2° | 16.0 |
| 14.8 ± 0.2° | 31.7 |
| 15.4 ± 0.2° | 74.0 |
| 16.1 ± 0.2° | 26.3 |
| 17.0 ± 0.2° | 50.9 |
| 17.8 ± 0.2° | 21.2 |
| 18.3 ± 0.2° | 21.9 |
| 20.4 ± 0.2° | 34.4 |
| 20.8 ± 0.2° | 16.1 |
| 21.6 ± 0.2° | 19.2 |
| 22.1 ± 0.2° | 34.6 |
| 22.8 ± 0.2° | 33.6 |
| 23.1 ± 0.2° | 21.6 |
| 23.8 ± 0.2° | 86.9 |
| 25.1 ± 0.2° | 21.0 |
| 25.4 ± 0.2° | 74.2 |
| 26.4 ± 0.2° | 40.5 |
| 26.9 ± 0.2° | 27.0 |
| 27.8 ± 0.2° | 15.6 |
| 28.8 ± 0.2° | 19.2. |

6. Compound A according to claim 3, wherein the Fourier IR spectrum of the crystalline form of compound A has characteristic peaks at wave number of 1650±2 $cm^{-1}$, 1507±2 $cm^{-1}$, 1422±2 $cm^{-1}$, 1395±2 $cm^{-1}$, 1371±2 $cm^{-1}$, 1274±2 $cm^{-1}$, 1252±2 $cm^{-2}$, 1226±2 $cm^{-1}$, 1145±2 $cm^{-1}$, 937±2 $cm^{-1}$, 877±2 $cm^{-1}$ and 756±2 $cm^{-1}$.

7. Compound A according to claim 3, wherein a single crystal of the crystalline form of compound A, measured at 106 K, belongs to the triclinic system with space group P1, and has the following unit cell parameters: a=8.6 Å±0.2 Å, b=9.0 Å±0.2 Å, c=17.3 Å±0.2 Å; and dihedral angles: α=84.0°±0.2°, β=77.4°±0.2°, γ=77.8°±0.2°.

8. A method of preparing compound A according to claim 1, comprising directly reacting fruquintinib with 0.67 to 3 equivalents of saccharin, in an organic solvent or a solvent combination, wherein the organic solvent is a solvent that can dissolve fruquintinib or saccharin.

9. A method of preparing the crystalline form of compound A according to claim 3, comprising any one of the following methods:
1) mixing fruquintinib and saccharin at a molar ratio of 1:0.67 to 1:1.5 in a solvent selected from the group consisting of a $C_1$ to $C_4$ alcohol, a $C_4$ to $C_5$ ester, a haloalkane, a $C_4$ to $C_6$ ether, a $C_3$ to $C_4$ ketone, acetonitrile, and any mixture thereof, for reaction, and removing the solvent to obtain the crystalline form of compound A;
the operation temperature of the preparation method is from 10 to 50° C.;
the crystallization time is from 8 to 48 hours;
the weight-to-volume ratio of fruquintinib to the solvent is from 5 mg:1 ml to 50 mg:1 ml; and
the weight-to-volume ratio of saccharin to the solvent is from 2 mg:1 ml to 20 mg:1 ml;
2) adding a solvent to the mixture of equal molar ratio of fruquintinib and saccharin, completely wetting the mixture, and grinding it until dry to obtain the crystalline form of compound A, wherein the solvent is selected from the group consisting of water, a $C_1$ to $C_4$ alcohol, a $C_4$ to $C_5$ ester, an alkane, a $C_4$ to $C_6$ ether, a $C_3$ to $C_4$ ketone, acetonitrile, and any mixture thereof;
the weight-to-volume ratio of the mixture to the solvent is from 20 mg:1 ml to 220 mg:1 ml; and
the operation temperature of the preparation method is from 10 to 40° C.; or
3) forming a solution of a mixture of equal molar ratio of fruquintinib and saccharin with mixed organic solvents, wherein the organic solvent is selected from the group consisting of a $C_1$ to $C_4$ alcohol, a $C_4$ to $C_5$ ether, a $C_4$ to $C_5$ ester, a haloalkane, a $C_3$ to $C_4$ ketone, acetonitrile, nitromethane, and any mixture thereof, volatilizing naturally for crystallization to obtain compound A crystalline form;
the operation temperature of the preparation method is from 10 to 50° C.; and
the weight-to-volume ratio of the mixture to the solvent is from 5 mg:1 ml to 50 mg:1 ml.

10. A cocrystal of fruquintinib and malonic acid having the structure shown below:

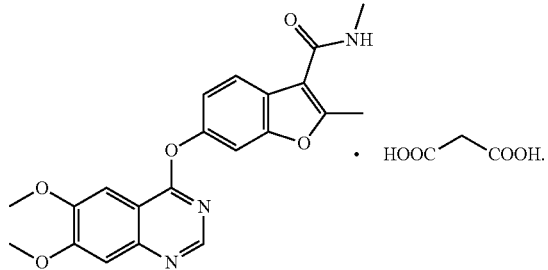

11. The cocrystal according to claim 10, wherein the X-ray powder diffraction pattern of the crystalline form of the cocrystal, expressed as 2θ angles, has the following characteristic peaks: 10.9±0.2°, 14.2±0.2°, 16.4±0.2° and 19.9±0.2°.

12. The cocrystal according to claim 11, wherein the X-ray powder diffraction pattern of the crystalline form of the cocrystal, expressed as 2θ angles, further comprises the following characteristic peaks: 9.8±0.2°, 11.6±0.2°, and 14.9±0.2°.

13. The cocrystal according to claim 12, wherein the X-ray powder diffraction pattern of the crystalline form of the cocrystal, expressed as 2θ angles, has the following characteristic peaks and relative intensities:

| 2θ | Relative intensity % |
| --- | --- |
| 5.3 ± 0.2° | 13.0 |
| 5.7 ± 0.2° | 37.3 |
| 9.8 ± 0.2° | 56.7 |
| 10.9 ± 0.2° | 100.0 |
| 11.6 ± 0.2° | 49.9 |
| 14.2 ± 0.2° | 62.0 |
| 14.9 ± 0.2° | 18.8 |
| 15.3 ± 0.2° | 29.6 |
| 16.4 ± 0.2° | 69.3 |
| 19.9 ± 0.2° | 71.7 |
| 22.1 ± 0.2° | 11.4 |
| 23.5 ± 0.2° | 10.3 |
| 25.0 ± 0.2° | 20.6 |
| 33.1 ± 0.2° | 10.6 |
| 37.8 ± 0.2° | 10.3. |

14. The cocrystal according to claim 11, wherein the Fourier IR spectrum of the crystalline form of the cocrystal has characteristic peaks at wave number of 1741±2 $cm^{-1}$, 1663±2 $cm^{-1}$, 1609±2 $cm^{-1}$, 1509±2 $cm^{-1}$, 1421±2 $cm^{-1}$, 1390±2 $cm^{-1}$, 1227±2 $cm^{-1}$, 1122±2 $cm^{-1}$, 983±2 $cm^{-1}$, 838±2 $cm^{-1}$ and 738±2 $cm^{-1}$.

15. A method of preparing the cocrystal according to claim 10, comprising directly reacting fruquintinib with 0.5 to 2.5 molar equivalents of malonic acid, in an organic solvent or solvent combination, wherein the organic solvent is a solvent that can dissolve fruquintinib or malonic acid.

16. A method of preparing the crystalline form of the cocrystal according to claim 11, comprising any one of the following preparation methods:
1) mixing fruquintinib and malonic acid at a molar ratio of 1:0.5 to 1:2 in a solvent selected from the group consisting of a $C_1$ to $C_4$ alcohol, a haloalkane, a $C_4$ to $C_6$ ether, a $C_3$ to $C_4$ ketone, acetonitrile, and any mixture thereof, for reaction, and removing the solvent to obtain the crystalline form of the cocrystal of fruquintinib and malonic acid;
the operation temperature of the preparation method is from 10 to 50° C.;
the crystallization time is from 8 to 48 hours;
the weight-to-volume ratio of fruquintinib to the solvent is from 5 mg:1 ml to 50 mg:1 ml; and
the weight-to-volume ratio of malonic acid to the solvent is from 1 mg:1 ml to 30 mg:1 ml;
2) adding a solvent to the mixture of equal molar ratio of fruquintinib and malonic acid, completely wetting the mixture, and grinding it until dry to obtain the crystalline form of the cocrystal of fruquintinib and malonic acid, wherein the solvent is selected from the group consisting of water, a $C_1$ to $C_4$ alcohol, a $C_4$ to $C_5$ ester, an alkane, a $C_4$ to $C_6$ ether, a $C_3$ to $C_4$ ketone, acetonitrile, and any mixture thereof;

the weight-to-volume ratio of the mixture to the solvent is from 20 mg:1 ml to 253 mg:1 ml; and the operation temperature of the preparation method is from 10 to 40° C.; or 3) forming a solution of a mixture of equal molar ration of fruquintinib and malonic acid with mixed organic solvents, wherein the organic solvent is selected from the group consisting of a $C_1$ to $C_4$ alcohol, a $C_4$ to $C_6$ ether, a haloalkane, a $C_3$ to $C_4$ ketone, acetonitrile, and any mixture thereof, volatilizing the solution naturally to crystallize to obtain the crystalline form of the cocrystal of fruquintinib and malonic acid;

the operation temperature of the preparation method is from 10 to 50° C.; and the weight-to-volume ratio of the mixture to the solvent is from 1 mg:1 ml to 50 mg:1 ml.

17. A cocrystal of fruquintinib and maleic acid having the structure shown below:

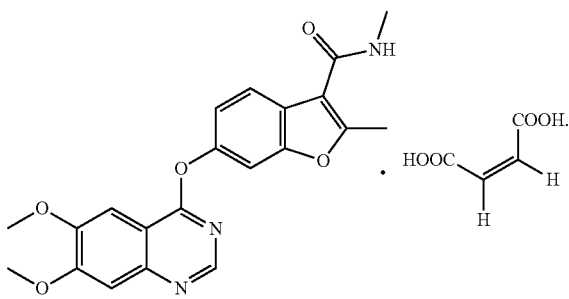

18. The cocrystal according to claim 17, wherein the X-ray powder diffraction pattern of the crystalline form of the cocrystal, expressed as 2θ angles, has the following characteristic peaks: 3.9±0.2°, 5.6±0.2°, 8.9±0.2° and 15.0±0.2°.

19. The cocrystal according to claim 18, wherein the X-ray powder diffraction pattern of the crystalline form of the cocrystal, expressed as 2θ angles, further comprises the following characteristic peaks: 8.4±0.2°, 11.4±0.2°, 17.6±0.2°, 23.4±0.2° and 27.4±0.2°.

20. The cocrystal according to claim 19, wherein the X-ray powder diffraction pattern of the crystalline form of the cocrystal, expressed as 2θ angles, has the following characteristic peaks and relative intensities:

| 2θ | Relative intensity % |
| --- | --- |
| 3.9 ± 0.2° | 20.9 |
| 5.6 ± 0.2° | 100.0 |
| 7.6 ± 0.2° | 13.8 |
| 8.4 ± 0.2° | 26.9 |
| 8.9 ± 0.2° | 55.6 |
| 10.8 ± 0.2° | 12.3 |
| 11.4 ± 0.2° | 27.7 |
| 12.7 ± 0.2° | 20.5 |
| 15.0 ± 0.2° | 60.3 |
| 16.2 ± 0.2° | 24.3 |
| 17.6 ± 0.2° | 29.7 |
| 23.4 ± 0.2° | 23.8 |
| 24.2 ± 0.2° | 26.5 |
| 24.9 ± 0.2° | 16.6 |
| 26.4 ± 0.2° | 23.4 |
| 27.4 ± 0.2° | 33.2 |
| 28.9 ± 0.2° | 14.5. |

21. The cocrystal according to claim 18, wherein the Fourier IR spectrum of the crystalline form of the cocrystal has characteristic peaks at wave number of 1627±2 $cm^{-1}$, 1510±2 $cm^{-1}$, 1422±2 $cm^{-1}$, 1398±2 $cm^{-1}$, 1233±2 $cm^{-1}$, 1126±2 $cm^{-1}$, 986±2 $cm^{-1}$, 861±2 $cm^{-1}$, and 650±2 $cm^{-1}$.

22. A method of preparing the cocrystal according to claim 17, comprising the method of directly reacting fruquintinib with 0.5 to 3 equivalents of maleic acid, in an organic solvent or solvent combination, wherein the organic solvent is a solvent that can dissolve fruquintinib or maleic acid.

23. A method of preparing the crystalline form of the cocrystal according to claim 18, comprising any one of the following methods:

1) mixing fruquintinib and maleic acid at a molar ratio of 1:0.5 to 1:1.5 in a solvent selected from the group consisting of a $C_1$ to $C_4$ alcohol, a haloalkane, a $C_3$ to $C_4$ ketone, acetonitrile, and any mixture thereof, for reaction, and removing the solvent to obtain the crystalline form of the cocrystal of fruquintinib and maleic acid;

the operation temperature of the preparation method is from 10 to 50° C.;

the crystallization time is from 8 to 48 hours;

the weight-to-volume ratio of fruquintinib to the solvent is from 5 mg:1 ml to 50 mg:1 ml; and the weight-to-volume ratio of maleic acid to the solvent is from 3 mg:1 ml to 20 mg:1 ml;

2) adding a solvent to the mixture of equal molar ratio of fruquintinib and maleic acid, completely wetting the mixture, and grinding it until dry to obtain the crystalline form of the cocrystal, wherein the solvent is selected from the group consisting of water, a $C_1$ to $C_4$ alcohol, a $C_4$ to $C_5$ ester, an alkane, a $C_4$ to $C_6$ ether, a $C_3$ to $C_4$ ketone, acetonitrile, and any mixture thereof;

the weight-to-volume ratio of the mixture to the solvent is from 20 mg:1 ml to 205 mg:1 ml; and the operation temperature of the preparation method is from 10 to 50° C.; or 3) forming a solution of a mixture of equal molar ratio of fruquintinib and maleic acid with mixed organic solvents, wherein the organic solvent is selected from the group consisting of a $C_1$ to $C_4$ alcohol, a $C_3$ to $C_4$ ketone, a cycloether, a haloalkane, acetonitrile, and any mixture thereof, volatilizing naturally for crystallization to obtain the crystalline form of the cocrystal of fruquintinib and maleic acid;

the operation temperature of the preparation method is from 10 to 50° C.; and the weight-to-volume ratio of the mixture to the solvent is from 1 mg:1 ml to 50 mg:1 ml.

24. A pharmaceutical composition comprising a therapeutically effective amount of compound A according to claim 1, and at least one pharmaceutically acceptable carrier or excipient.

25. A method for treating a disease in a patient, wherein the method comprises administering to the patient in need thereof a therapeutically effective amount of compound A according to claim 1, or a pharmaceutical composition thereof, wherein the disease is associated with abnormal angiogenesis in the patient; and wherein the disease is selected from the group consisting of cancer, tumor, macular lesion, and chronic inflammatory disease.

26. A pharmaceutical composition comprising a therapeutically effective amount of the cocrystal of fruquintinib and malonic acid according to claim 10, and at least one pharmaceutically acceptable carrier or excipient.

27. A method for treating a disease in a patient, wherein the method comprises administering to the patient in need thereof a therapeutically effective amount of the cocrystal of fruquintinib and malonic acid according to claim 10, or a pharmaceutical composition thereof, wherein the disease is associated with abnormal angiogenesis in the patient; and wherein the disease is selected from the group consisting of cancer, tumor, macular lesion, and chronic inflammatory disease.

28. A pharmaceutical composition comprising a therapeutically effective amount of the cocrystal of fruquintinib and maleic acid according to claim 17, and at least one pharmaceutically acceptable carrier or excipient.

29. A method for treating a disease in a patient, wherein the method comprises administering to the patient in need thereof a therapeutically effective amount of the cocrystal of fruquintinib and maleic acid according to claim 17, or a pharmaceutical composition thereof, wherein the disease is associated with abnormal angiogenesis in the patient; and wherein the disease is selected from the group consisting of cancer, tumor, macular lesion, and chronic inflammatory disease.

* * * * *